United States Patent
Beller et al.

(10) Patent No.: US 10,975,009 B2
(45) Date of Patent: *Apr. 13, 2021

(54) SELECTIVE REDUCTION OF ALDEHYDES AND KETONES

(71) Applicant: DSM IP ASSETS B.V., Heerlen (NL)

(72) Inventors: Matthias Beller, Rostock (DE); Werner Bonrath, Kaiseraugst (CH); Johannes Gerardus De Vries, Rostock (DE); Yuting Fan, Rostock (DE); Sandra Hinze, Rostock (DE); Laurent Lefort, Kaiseraugst (CH); Jonathan Alan Medlock, Kaiseraugst (CH); Pim Puylaert, Rostock (DE); Richard Van Heck, Rostock (DE)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/300,944

(22) PCT Filed: May 11, 2017

(86) PCT No.: PCT/EP2017/061298
§ 371 (c)(1),
(2) Date: Nov. 12, 2018

(87) PCT Pub. No.: WO2017/194662
PCT Pub. Date: Nov. 16, 2017

(65) Prior Publication Data
US 2019/0300462 A1 Oct. 3, 2019

(30) Foreign Application Priority Data

May 13, 2016 (EP) ..................... 16169508
Jan. 23, 2017 (EP) ..................... 17152590

(51) Int. Cl.
| | |
|---|---|
| *C07C 29/143* | (2006.01) |
| *C07C 29/145* | (2006.01) |
| *B01J 31/22* | (2006.01) |
| *B01J 31/24* | (2006.01) |
| *C07D 307/83* | (2006.01) |
| *B01J 31/18* | (2006.01) |
| *C07C 29/141* | (2006.01) |
| *C07D 307/42* | (2006.01) |
| *C07D 213/38* | (2006.01) |
| *C07D 307/44* | (2006.01) |
| *C07D 215/12* | (2006.01) |
| *B01J 31/02* | (2006.01) |

(52) U.S. Cl.
CPC ......... *C07C 29/145* (2013.01); *B01J 31/1815* (2013.01); *B01J 31/226* (2013.01); *B01J 31/2404* (2013.01); *C07C 29/141* (2013.01); *C07D 213/38* (2013.01); *C07D 215/12* (2013.01); *C07D 307/42* (2013.01); *C07D 307/44* (2013.01); *C07D 307/83* (2013.01); *B01J 31/0212* (2013.01); *B01J 2231/643* (2013.01); *B01J 2531/0238* (2013.01); *B01J 2531/0258* (2013.01); *B01J 2531/821* (2013.01); *B01J 2531/825* (2013.01); *B01J 2531/842* (2013.01); *B01J 2531/845* (2013.01); *C07C 2601/16* (2017.05)

(58) Field of Classification Search
CPC .................................... C07C 29/143
See application file for complete search history.

(56) References Cited

U.S. PATENT DOCUMENTS 10,370,314 B2 * 8/2019 Beller .................. B01J 31/2404

OTHER PUBLICATIONS

Singh, R., et al. "Iron(III) complexes using NNS reduced Schiff bases and NNOS coordinating tetradentate ligands: Synthesis, structure and catecholase activity." Inorganica Chimica Acta (2010), vol. 363, pp. 3131-3138. (Year: 2010).*
Tang, L., et al. "A new chiral sulfinyl-NH-pyridine ligand for Ir-catalyzed asymmetric transfer hydrogenation reaction." Tetrahydeon Letters. (2012), vol. 53, pp. 3839-384. (Year: 2012).*
Sunghee Kim, et al., "Tuning of the Copper-Thioether Bond in Tetradentate $N_3S_{(thioether)}$ Ligands; O—O Bond Reductive Cleavage via a $[Cu^{II}_2(\mu\text{-}1,2\text{-peroxo})]^{2+}/[Cu^{III}_2(\mu\text{-oxo})_2]^{2+}$ Equilibrium", Journal of the American Chemical Society, vol. 136, No. 22, May 22, 2014, pp. 8063-8071. (9 pages).
Neva Lazarova, et al., "Thiol- and Thioether-Based Bifunctional Chelates for the $\{M(CO)_3\}^+$Core (M=Tc, Re)", Inorganic Chemistry, vol. 44, No. 19, Aug. 17, 2005, pp. 6763-6770. (8 pages).
Dong-Heon Lee, et al., "Copper(I) Complex $O_2$-Reactivity with a $N_3S$ Thioether Ligand: a Copper-Dioxygen Adduct Including Sulfur Ligation, Ligand Oxygenation, and Comparisons with All Nitrogen Ligand Analogues", Inorganic Chemistry, vol. 46, No. 15, Jun. 20, 2007, pp. 6056-6068. (13 pages).
Magdalena M. Makowska-Grzyska, et al., "Modeling Substrate- and Inhibitor-Bound Forms of Liver Alcohol Dehydrogenase: Chemistry of Mononuclear Nitrogen/Sulfur-Ligated Zinc Alcohol, Formamide, and Sulfoxide Complexes", Inorganic Chemistry, vol. 41, No. 19, Aug. 20, 2002, pp. 4872-4887. (16 pages).
Reena Singh, et al., "Iron(III) complexes using NNS reduced Schiff bases and NNOS coordinating tetradentate ligands: Synthesis, structure and catecholase activity", Inorganica Chimica Acta, vol. 363, No. 12, Oct. 15, 2010, pp. 3131-3138. (8 pages).
Lei Tang, et al., "A new chiral sulfinyl-NH-pyridine ligand for Ir-catalyzed asymmetric transfer hydrogenation reaction", Tetrahedron Letters, ElSevier, vol. 53, No. 30, Apr. 24, 2012, pp. 3839-3842. (4 pages).
International Search Report for PCT/EP2017/061298 dated Jul. 26, 2017. (3 pages).
Written Opinion of the ISA for PCT/EP2017/061298 dated Jul. 26, 2017. (7 pages).
Puylaert, P. et al, *Selective Hydrogenation of α,β-Unsaturated Aldehydes and Ketones by Air-Stable Ruthenium NNS Complexes*, Chem.Eur.J, 2017, 23, 8473-8481.

(Continued)

*Primary Examiner* — John S Kenyon
(74) *Attorney, Agent, or Firm* — Nixon & Vanderhye P.C.

(57) ABSTRACT

The present invention relates to a selective reduction of specific aldehydes and ketones to their corresponding alcohols.

17 Claims, No Drawings

(56) References Cited

OTHER PUBLICATIONS

EP Appln. 17721851.0-1109, Communication Pursuant to Article 94(3) EPC, dated Jan. 23, 2020.
Notice of Reasons of Rejection, JP Application No. P2018-555885, dated Dec. 22, 2020.
Inorganica Chimica Acta, 2010, 363(12), 3131-3138.
Bulletin of the Chemical Society of Japan, 1999, 72(3), 415-424.
Registry(STN)[online], 2004, 10. 10, CAS Registration No. 759443-52-2.
Main Group Chemistry, 2007, 6(3 & 4), 155-168.

* cited by examiner

SELECTIVE REDUCTION OF ALDEHYDES AND KETONES

This application is the U.S. national phase of International Application No. PCT/EP2017/061298 filed May 11, 2017 which designated the U.S. and claims priorities to EP 16169508.5 filed May 13, 2016, and EP17152590.0 filed Jan. 23, 2017, the entire contents of each of which are hereby incorporated by reference.

The present invention relates to a selective reduction of specific aldehydes and ketones to their corresponding alcohols.

Reduction of an aldehyde or ketone into the corresponding alcohol is a fundamental and very important reaction in organic chemistry, and it is used in a large number of chemical processes. The obtained alcohols are used as such or are important intermediates in further chemical processes.

A convenient manner to achieve such reduction is to use a hydrogenation process. The hydrogenation process can be carried out with $H_2$ gas or as a transfer hydrogenation. Therefore, in the context of the present invention the term "hydrogenation" (if not otherwise stated) covers the hydrogenations with $H_2$ gas as well as the transfer hydrogenations.

The specific aldehydes and ketones which are reduced in the context of the present invention are α,β-unsaturated aldehydes and ketones. These aldehydes and ketones have the following general formula (I)

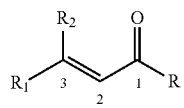

(I)

wherein R is H (aldehydes) or an alkyl group (ketones), and $R_1$ and $R_2$ can be a suitable organic moiety (which are defined below).

The problem of the hydrogenation of compounds of formula (I) is that (at least) two sites could be hydrogenated. Either the =O group or the C—C double bond (or both).

Therefore it is possible that a variety of hydrogenated products can be obtained (in any kind of mixture). Mainly the following compounds are obtained:

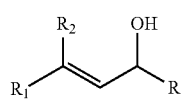

(IIa)

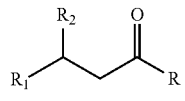

(IIb)

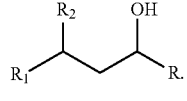

(IIc)

The problem is that when a mixture of such compounds is obtained, a separation step needs to be carried out. Additionally, the yield of the desired alcohol is usually low.

Now, the goal of the present invention was to find a way that a selective reduction (hydrogenation) of specific aldehydes and ketones can be achieved, wherein mainly compounds of the general formula (IIa) are obtained in excellent yield and selectivity.

The specific aldehydes and ketones, which are of interest in the context of the present patent application are those of formula (I)

(I)

wherein
R is H or a $C_1$-$C_4$ alkyl group, or R forms together with carbon atom (2) a 4 to 8 membered aliphatic ring system, which can be substituted; and
$R_1$ is H; an aromatic ring system which is unsubstituted or an aromatic ring system which is substituted; a heteroaromatic ring system which is unsubstituted or a heteroaromatic ring system which is substituted; an aliphatic ring system which is unsubstituted or an aliphatic ring system which is substituted; a heteroaliphatic ring system which is unsubstituted or a heteroaliphatic ring system which is substituted; —$CH_3$; —$CH_2CH_3$; a $C_3$-$C_{10}$ alkyl group, which can be linear or branched and which can be partially unsaturated (comprising C—C double bond(s)) or a $C_{11}$-$C_{20}$ alkyl group, which can be linear or branched and which can be partially unsaturated (comprising C—C double bond(s));
or $R_1$ forms together with the C—C double bond of formula (I) a 5 to 8 membered aliphatic ring system, which can be substituted or a 5 to 8 membered aromatic ring system, which can be substituted;
or $R_1$ forms together with the C—C double bond of formula (I) a 5 to 8 membered heteroaliphatic ring system, which can be substituted or a 5 to 8 membered aromatic ring system, which can be substituted
or $R_1$ forms together with the C—C double bond of formula (I) a 5 to 8 membered aromatic ring system, which can be substituted or a 5 to 8 membered aromatic ring system, which can be substituted
or $R_1$ forms together with the C—C double bond of formula (I) a 5 to 8 membered heteroaromatic ring system, which can be substituted or a 5 to 8 membered aromatic ring system, which can be substituted;
or R and $R_1$ form together a 3 to 8 membered aliphatic ring system, which can be substituted; and
$R_2$ is H; —$CH_3$; —$CH_2CH_3$; or a $C_3$-$C_{10}$ alkyl group, which can be linear or branched and which can be partially unsaturated (comprising C—C double bond(s)).

The corresponding alcohols, which are the selectively hydrogenated products are those of formula (IIa)

(IIa)

wherein the substituents have the same definition as in formula (I).

Surprisingly it was found that by the use of new specific catalysts it is possible to reduce the compounds of formula (I) selectively in excellent yield and selectivity under mild reaction conditions.

The catalysts, which are used in the selective reduction (hydrogenation) according to the present invention are transition metal catalysts of formula (III)

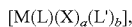  (III)

wherein
M is a transition metal (preferably a transition metal chosen from the group consisting of Os, Co, Ru and Fe, more preferably from the group consisting of Ru and Fe) and
X is an anion (preferably a halogen anion, a carboxylate (such as acetate or benzoate), borohydride (such as $BH_4^-$), hydride, $BF_4^-$, or $PF_6^-$, more preferably a halogen anion, most preferably $Cl^-$), and
L' is a monodentate ligand (preferably a monodentate phosphine ligand, more preferably triphenylphosphine (=$PPh_3$)), and
L is a tridentate ligand (which means that the ligand can be bound to the M at up to three sites) of formula (IV)

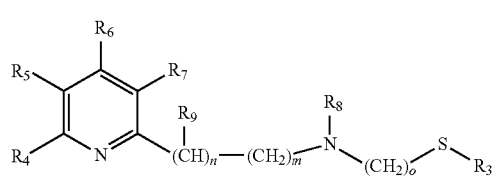  (IV)

wherein
$R_3$ is a linear $C_1$-$C_4$ alkyl group, which can be substituted; a branched $C_3$-$C_4$ alkyl group, which can be substituted; or a phenyl group, which can be substituted, and
$R_4$ is H; a linear $C_1$-$C_4$ alkyl group, which can be substituted; a branched $C_3$-$C_4$ alkyl group, which can be substituted; or $OC_1$-$C_2$alkyl, and
$R_5$ is H; a linear $C_1$-$C_4$ alkyl group, which can be substituted; a branched $C_3$-$C_4$ alkyl group, which can be substituted; or $OC_1$-$C_2$alkyl, and
or $R_4$ and $R_5$ form a $C_4$-$C_8$ ring system, which can be aliphatic or aromatic, and
$R_6$ is H; a linear $C_1$-$C_4$ alkyl group, which can be substituted; a branched $C_3$-$C_4$ alkyl group, which can be substituted; or $OC_1$-$C_2$alkyl, and
$R_7$ is H; a linear $C_1$-$C_4$ alkyl group, which can be substituted; a branched $C_3$-$C_4$ alkyl group, which can be substituted; or $OC_1$-$C_2$alkyl, and
$R_8$ is H or a a linear $C_1$-$C_4$ alkyl group, which can be substituted; a branched $C_3$-$C_4$ alkyl group, which can be substituted, and
$R_9$ is —$CH_3$ or —$CH_2CH_3$, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2, 3 or 4.

From the state of the art, it is known that transition metal complexes can exist as monomers as well as dimers or even as oligomers. The present formula (III) defines the empirical formula of the catalyst.

Therefore the present invention relates to a process (P) of production of a compound of formula (IIa)

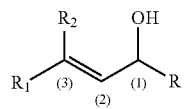  (IIa)

wherein
R is H or a $C_1$-$C_4$ alkyl group, or
R forms together with carbon atom (2) a 4 to 8 membered aliphatic ring system, which can be substituted; and
$R_1$ is H; an aromatic ring system which is unsubstituted or an aromatic ring system which is substituted; a heteroaromatic ring system which is unsubstituted or a heteroaromatic ring system which is substituted; an aliphatic ring system which is unsubstituted or an aliphatic ring system which is substituted; a heteroaliphatic ring system which is unsubstituted or a heteroaliphatic ring system which is substituted; —$CH_3$; —$CH_2CH_3$; a $C_3$-$C_{10}$ alkyl group, which can be linear or branched and which can be partially unsaturated (comprising C—C double bond(s)) or a $C_{11}$-$C_{20}$ alkyl group, which can be linear or branched and which can be partially unsaturated (comprising C—C double bond(s))
or $R_1$ forms together with the C—C double bond of formula (IIa) a 5 to 8 membered aliphatic ring system, which can be substituted or a 5 to 8 membered aromatic ring system, which can be substituted;
or $R_1$ forms together with the C—C double bond of formula (IIa) a 5 to 8 membered heteroaliphatic ring system, which can be substituted or a 5 to 8 membered aromatic ring system, which can be substituted
or $R_1$ forms together with the C—C double bond of formula (IIa) a 5 to 8 membered aromatic ring system, which can be substituted or a 5 to 8 membered aromatic ring system, which can be substituted
or $R_1$ forms together with the C—C double bond of formula (IIa) a 5 to 8 membered heteroaromatic ring system, which can be substituted or a 5 to 8 membered aromatic ring system, which can be substituted;
or R and $R_1$ form together a 3 to 8 membered aliphatic ring system, which can be substituted; and
$R_2$ is H; —$CH_3$; —$CH_2CH_3$; or a $C_3$-$C_{10}$ alkyl group, which can be linear or branched and which can be partially unsaturated (comprising C—C double bond(s))
by a selective reduction of a compound of formula (I)

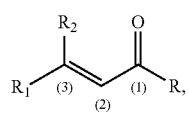  (I)

wherein the R, $R_1$ and $R_2$ have the same meaning as defined in the compound of formula (IIa),
characterised in, that the selective reduction is carried out in the presence of at least one transition metal catalyst of formula (III)

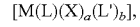  (III)

wherein
M is a transition metal and
X is an anion, and
L' is a monodentate ligand, and
L is a tridentate ligand of formula (IV)

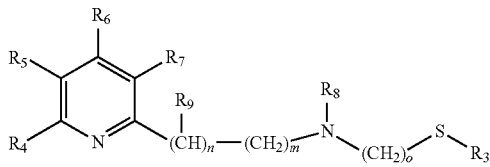

(IV)

wherein
R₃ is a linear $C_1$-$C_4$ alkyl group, which can be substituted; a branched $C_3$-$C_4$ alkyl group, which can be substituted; or a phenyl group, which can be substituted, and R₄ is H; a linear $C_1$-$C_4$ alkyl group, which can be substituted; a branched $C_3$-$C_4$ alkyl group, which can be substituted; or $OC_1$-$C_2$alkyl, and R₅ is H; a linear $C_1$-$C_4$ alkyl group, which can be substituted; a branched $C_3$-$C_4$ alkyl group, which can be substituted; or $OC_1$-$C_2$alkyl, and or R₄ and R₅ form a $C_4$-$C_8$ ring system, which can be aliphatic or aromatic, and R₆ is H; a linear $C_1$-$C_4$ alkyl group, which can be substituted; a branched $C_3$-$C_4$ alkyl group, which can be substituted; or $OC_1$-$C_2$alkyl, and R₇ is H; a linear $C_1$-$C_4$ alkyl group, which can be substituted; a branched $C_3$-$C_4$ alkyl group, which can be substituted; or $OC_1$-$C_2$alkyl, and R₈ is H or a a linear $C_1$-$C_4$ alkyl group, which can be substituted; a branched $C_3$-$C_4$ alkyl group, which can be substituted, and R₉ is —CH₃ or —CH₂CH₃, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2, 3 or 4.

The process according to the present invention is preferably carried out in the presence of at least one base.

Preferably the base has the following formula (VIII)

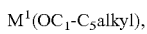

wherein M¹ is an alkali metal.

Preferred is a base of formula (VIII'),

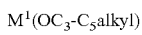

wherein
M¹ is Li, Na or K.

Especially preferred bases are selected from the group consisting of KOtBu, NaOtBu and LiOtBu.

Therefore the present invention relates to a process (P1), which is process (P), wherein the process is carried out in the presence of at least one base.

Therefore the present invention relates to a process (P1'), which is process (P1), wherein the process is carried out in the presence of at least one base of formula (VIII)

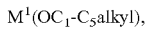

wherein M¹ is an alkali metal.

Therefore the present invention relates to a process (P1''), which is process (P1), wherein the process is carried out in the presence of at least one base of formula (VIII'),

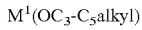

wherein
M¹ is Li, Na or K.

Therefore the present invention relates to a process (P1'''), which is process (P1), wherein the process is carried out in the presence of at least one base selected from the group consisting of KOtBu, NaOtBu and LiOtBu.

The amount of the base can vary. Usually and preferably the base (or mixture of bases) is used in an amount of 0.1-5 mol-% (based on the number of moles of the compound of formula (I)).

Therefore the present invention relates to a process (P1''''), which is process (P1), (P1'), (P1'') or (P1'''), wherein 0.1-5 mol-% (based on the number of moles of the compound of formula (I)) of at least one base is used.

The catalyst of the present invention which is used to selectively reduce the compound of formula (I) is a compound of formula (III) as defined above.

In a preferred embodiment the following catalysts are used:

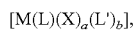 (III)

wherein
M is a transition metal chosen from the group consisting of Os, Co, Ru and Fe, and
X is a halogen anion, a carboxylate (such as acetate or benzoate), borohydride (such as $BH_4^-$), hydride, $BF_4^-$ or $PF_6^-$, and
L' is a monodentate phosphine ligand, and
L is a tridentate ligand of formula (IV)

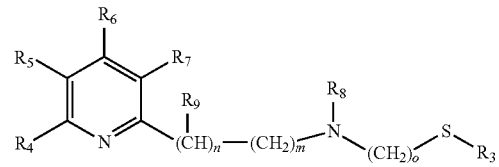

(IV)

wherein
R₃ is —CH₃ or —CH₂CH₃, and
R₄ is H; —CH₃; —CH₂CH₃; —OCH₃ or —OCH₂CH₃, and
R₅ is H; —CH₃; —CH₂CH₃; —OCH₃ or —OCH₂CH₃, and
or R₄ and R₅ form a $C_4$-$C_8$ ring system, which can be aliphatic or aromatic, and
R₆ is H; —CH₃; —CH₂CH₃; —OCH₃ or —OCH₂CH₃, and
R₇ is H; —CH₃; —CH₂CH₃; —OCH₃ or —OCH₂CH₃, and
R₈ is H; —CH₃ or —CH₂CH₃, and
R₉ is —CH₃ or —CH₂CH₃, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2 or 3.

In a more preferred embodiment the following catalysts are used:

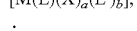 (III)

wherein
M is a transition metal chosen from the group consisting of Ru and Fe, and
X is a halogen anion (preferably Cl⁻), and
L' is triphenylphosphine, and L is a tridentate ligand of formula (IV)

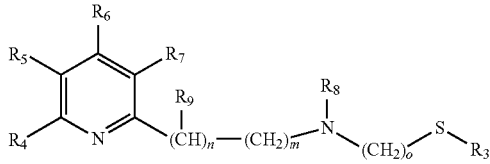
(IV)

wherein
R$_3$ is —CH$_3$ or —CH$_2$CH$_3$, and
R$_4$ is H; —CH$_3$; —CH$_2$CH$_3$; —OCH$_3$ or —OCH$_2$CH$_3$, and
R$_5$ is H or —CH$_3$, and
or R$_4$ and R$_5$ form a C$_4$-C$_8$ ring system, which can be aliphatic or aromatic, and
R$_6$ is H or —CH$_3$, and
R$_7$ is H or —CH$_3$, and
R$_8$ is H or —CH$_3$, and
R$_9$ is —CH$_3$, and
m is 0 or 1 and
n is 0 or 1,
with the proviso that the sum of m+n is 1,
o is 2,
a is 1 or 2,
b is 1 or 2,
with the proviso that the sum of a+b is 3.

In an especially preferred embodiment the following catalysts of formula (III')

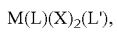  (III')

wherein
M is Ru or Fe, and
X is Cl$^-$, and
L' is PPh$_3$, and
L is a tridentate ligand chosen from the group consisting of the ligands of formulae (IVa)-(IVl)

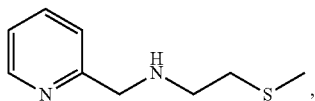
(IVa)

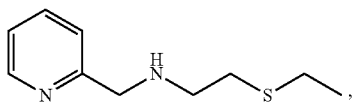
(IVb)

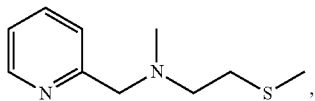
(IVc)

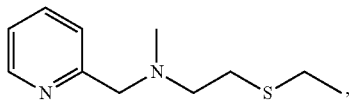
(IVd)

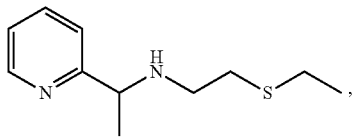
(IVe)

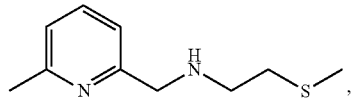
(IVf)

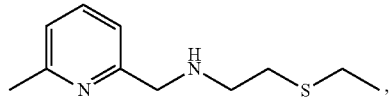
(IVg)

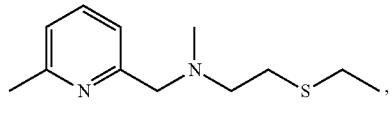
(IVh)

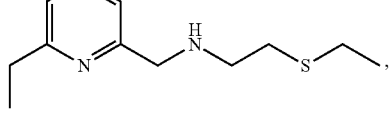
(IVi)

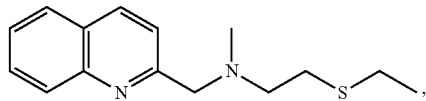
(IVj)

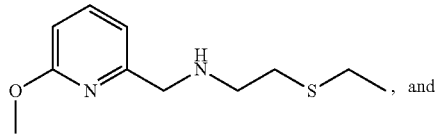
(IVk)

, and

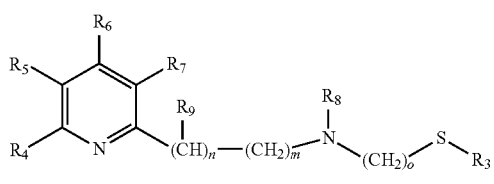
(IVl)

are used.

Therefore the present invention relates to a process (P2), which is process (P), (P1), (P1'), (P1''), (P1''') or (P1''''), wherein the following catalysts of formula (III)

[M(L)(X)$_a$(L')$_b$],  (III)

wherein
M is a transition metal chosen from the group consisting of Os, Co, Ru and Fe, and X is a halogen anion, a carboxylate (such as acetate or benzoate), borohydride (such as BH$_4^-$), hydride, BF$_4^-$ or PF$_6^-$, and
L' is a monodentate phosphine ligand, and
L is a tridentate ligand of formula (IV)

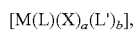
(IV)

wherein
R$_3$ is —CH$_3$ or —CH$_2$CH$_3$, and
R$_4$ is H; —CH$_3$; —CH$_2$CH$_3$; —OCH$_3$ or —OCH$_2$CH$_3$, and
R$_5$ is H; —CH$_3$; —CH$_2$CH$_3$; —OCH$_3$ or —OCH$_2$CH$_3$, and
or R$_4$ and R$_5$ form a C$_4$-C$_8$ ring system, which can be aliphatic or aromatic, and $R_6$ is H; —$CH_3$; —$CH_2CH_3$; —$OCH_3$ or —$OCH_2CH_3$, and
$R_7$ is H; —$CH_3$; —$CH_2CH_3$; —$OCH_3$ or —$OCH_2CH_3$, and
$R_8$ is H; —$CH_3$ or —$CH_2CH_3$, and
$R_9$ is —$CH_3$ or —$CH_2CH_3$, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2 or 3,
are used.

Therefore the present invention relates to a process (P2'), which is process (P), (P1), (P1'), (P1"), (P1''') or (P1''''), wherein the following catalysts of formula (III)

$$[M(L)(X)_a(L')_b], \quad (III)$$

wherein
M is a transition metal chosen from the group consisting of Ru and Fe, and
X is a halogen anion (preferably Cl⁻), and
L' is triphenylphosphine, and
L is a tridentate ligand of formula (IV)

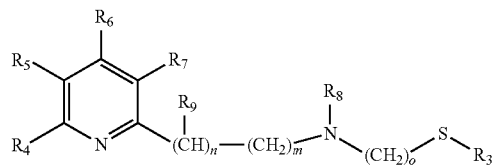
(IV)

wherein
$R_3$ is —$CH_3$ or —$CH_2CH_3$, and
$R_4$ is H; —$CH_3$; —$CH_2CH_3$; —$OCH_3$ or —$OCH_2CH_3$, and
$R_5$ is H or —$CH_3$, and
or $R_4$ and $R_5$ form a $C_4$-$C_8$ ring system, which can be aliphatic or aromatic, and
$R_6$ is H or —$CH_3$, and
$R_7$ is H or —$CH_3$, and
$R_8$ is H or —$CH_3$, and
$R_9$ is —$CH_3$, and
m is 0 or 1, and
n is 0 or 1,
with the proviso that the sum of m+n is 1,
o is 2,
a is 1 or 2,
b is 1 or 2,
with the proviso that the sum of a+b is 3,
are used.

Therefore the present invention relates to a process (P2"), which is process (P), (P1), (P1'), (P1"), (P1''') or (P1''''), wherein the following catalysts of formula (III')

$$M(L)(X)_2(L'), \quad (III')$$

wherein
M is Ru or Fe, and
X is Cl⁻, and
L' is PPh₃, and
L is a tridentate ligand chosen from the group consisting of the ligands of formulae (IVa)-(IVl)

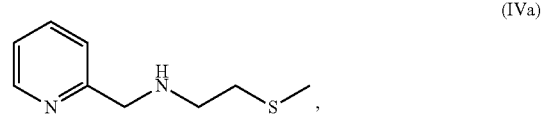 (IVa)

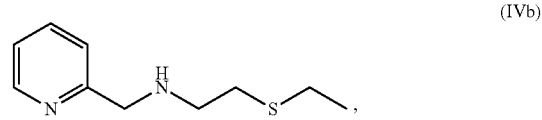 (IVb)

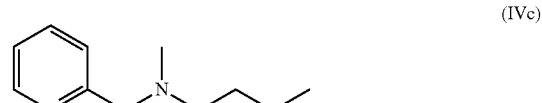 (IVc)

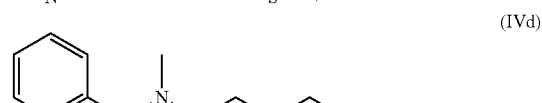 (IVd)

 (IVe)

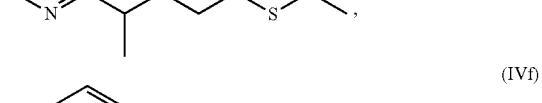 (IVf)

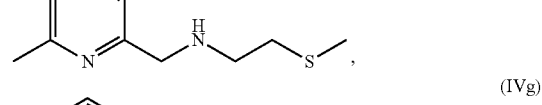 (IVg)

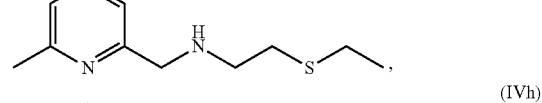 (IVh)

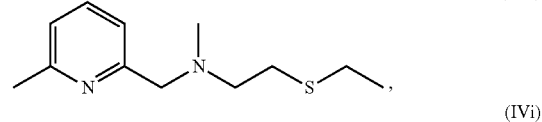 (IVi)

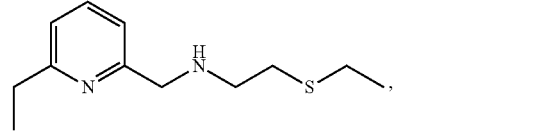 (IVj)

 (IVk)

, and

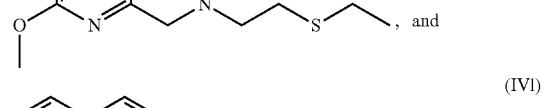 (IVl)

are used.

A preferred embodiment of the present invention also relates to a process (P3), which is process (P), (P1), (P1'), (P1"), (P1'''), (P1''''), (P2), (P2') or (P2"), wherein a compound of the formula (IIa)

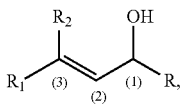

(IIa)

wherein
R is H or —CH$_3$; and
R$_1$ is an aromatic ring system which is unsubstituted or an aromatic ring system which is substituted; a heteroaromatic ring system which is unsubstituted or a heteroaromatic ring system which is substituted; an aliphatic ring system which is unsubstituted or an aliphatic ring system which is substituted; a heteroaliphatic ring system which is unsubstituted or a heteroaliphatic ring system which is substituted;
and
R$_2$ is H or —CH$_3$,
is produced Another preferred embodiment of the present invention also relates to a process (P3'), which is process (P3), wherein a compound of the formula (IIa')

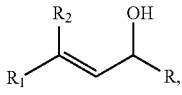

(IIa')

wherein
R is H or —CH$_3$ and
and
R$_1$ is benzene ring which is unsubstituted or a benzene ring which is substituted or furan ring which is unsubstituted or a furan ring which is substituted; hexane ring which is unsubstituted or a hexane ring which is substituted; a hexene ring which is unsubstituted or a hexene ring system which is substituted
R$_2$ is H or —CH$_3$,
is produced.

Another preferred embodiment of the present invention also relates to a process (P4), which is process (P), (P1), (P1'), (P1''), (P1'''), (P1''''), (P2), (P2') or (P2''), wherein a compound of the formula (IIa)

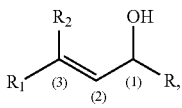

(IIa)

wherein
R is H or —CH$_3$; and
R$_1$ is an unsubstituted C$_3$-C$_8$ alkyl group, which can be linear or branched and which can be partially unsaturated or an unsubstituted C$_{12}$-C$_{18}$ alkyl group, which can be linear or branched and which can be partially unsaturated,
R$_2$ is H or —CH$_3$,
is produced.

Another preferred embodiment of the present invention also relates to a process (P5), which is process (P), (P1), (P1'), (P1''), (P1'''), (P1''''), (P2), (P2') or (P2''), wherein a compound of the formula (IIa)

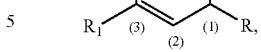

(IIa)

wherein
R is H or —CH$_3$; and
R$_1$ forms together with the C—C double bond of formula (IIa) a 5 to 8 membered aliphatic ring system, which can be substituted or a 5 to 8 membered aromatic ring system, which can be substituted;
or R$_1$ forms together with the C—C double bond of formula (IIa) a 5 to 8 membered heteroaliphatic ring system, which can be substituted or a 5 to 8 membered aromatic ring system, which can be substituted
or R$_1$ forms together with the C—C double bond of formula (IIa) a 5 to 8 membered aromatic ring system, which can be substituted or a 5 to 8 membered aromatic ring system, which can be substituted
or R$_1$ forms together with the C—C double bond of formula (IIa) a 5 to 8 membered heteroaromatic ring system, which can be substituted or a 5 to 8 membered aromatic ring system, which can be substituted and
R$_2$ is H or —CH$_3$,
is produced.

Another preferred embodiment of the present invention also relates to a process (P5), which is process (P), (P1), (P1'), (P1''), (P1'''), (P1''''), (P2), (P2') or (P2''), wherein a compound of the formula (IIa)

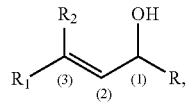

(IIa)

wherein
R forms together with carbon atom (2) a 4 to 8 membered aliphatic ring system, which can be substituted; and
and
R$_1$ forms together with the C—C double bond of formula (IIa) a 5 to 8 membered aliphatic ring system, which can be substituted or a 5 to 8 membered aromatic ring system, which can be substituted;
and
R$_2$ is H or —CH$_3$,
is produced.

Another preferred embodiment of the present invention also relates to a process (P5'), which is process (P5), wherein a compound of the formula (IIa')

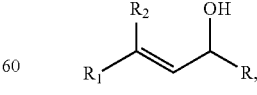

(IIa')

wherein
R is H or —CH$_3$ and
R$_1$ is H; benzene ring which is unsubstituted or a benzene ring system which is substituted; and
R$_2$ is H or —CH$_3$,
is produced.

A preferred embodiment of the present invention also relates to a process (P6), which is process (P), (P1), (P1'), (P1''), (P1'''), (P1''''), (P2), (P2') or (P2''), wherein any compound of formula (IIa¹) to (IIa¹²)

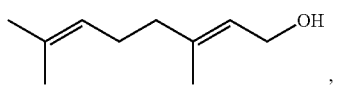 (IIa¹)

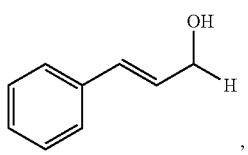 (IIa²)

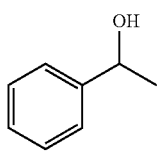 (IIa³)

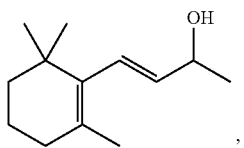 (IIa⁴)

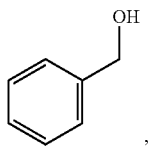 (IIa⁵)

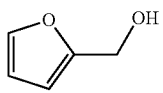 (IIa⁶)

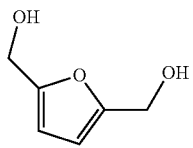 (IIa⁷)

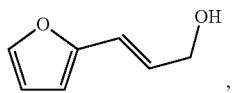 (IIa⁸)

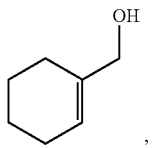 (IIa⁹)

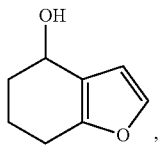 (IIa¹⁰)

-continued

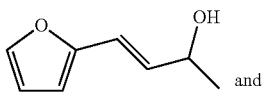 (IIa¹¹)

and

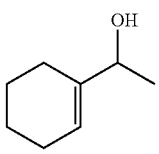 (IIa¹²)

is produced.

The catalysts of the present invention are also new.

Therefore the present invention also relates to a catalyst (C) of formula (III)

$$[M(L)(X)_a(L')_b],$$ (III)

wherein
M is a transition metal and
X is an anion, and
L' is a monodentate ligand, and
L is a tridentate ligand of formula (IV)

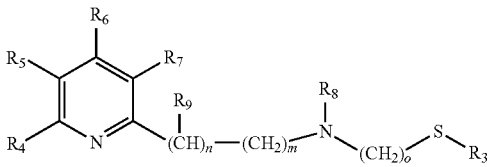 (IV)

wherein
$R_3$ is a linear $C_1$-$C_4$ alkyl group, which can be substituted; a branched $C_3$-$C_4$ alkyl group, which can be substituted; or a phenyl group, which can be substituted, and
$R_4$ is H; a linear $C_1$-$C_4$ alkyl group, which can be substituted; a branched $C_3$-$C_4$ alkyl group, which can be substituted; or $OC_1$-$C_2$alkyl, and
$R_5$ is H; a linear $C_1$-$C_4$ alkyl group, which can be substituted; a branched $C_3$-$C_4$ alkyl group, which can be substituted; or $OC_1$-$C_2$alkyl, and
or $R_4$ and $R_5$ form a $C_4$-$C_8$ ring system, which can be aliphatic or aromatic, and
$R_6$ is H; a linear $C_1$-$C_4$ alkyl group, which can be substituted; a branched $C_3$-$C_4$ alkyl group, which can be substituted; or $OC_1$-$C_2$alkyl, and
$R_7$ is H; a linear $C_1$-$C_4$ alkyl group, which can be substituted; a branched $C_3$-$C_4$ alkyl group, which can be substituted; or $OC_1$-$C_2$alkyl, and
$R_8$ is H or a a linear $C_1$-$C_4$ alkyl group, which can be substituted; a branched $C_3$-$C_4$ alkyl group, which can be substituted, and
$R_9$ is —$CH_3$ or —$CH_2CH_3$, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2, 3 or 4.

Therefore the present invention also relates to a catalyst (C') of formula (III)

$$[M(L)(X)_a(L')_b],$$ (III)

wherein
M is a transition metal chosen from the group consisting of Os, Co, Ru and Fe, and
X is a halogen anion, a carboxylate (such as acetate or benzoate), borohydride (such as $BH_4^-$), hydride, $BF_4^-$ or $PF_6^-$, and
L' is a monodentate phosphine ligand, and
L is a tridentate ligand of formula (IV)

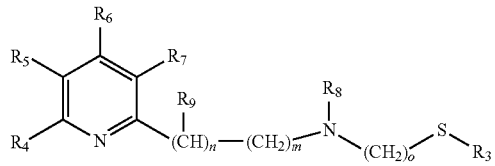

(IV)

wherein
$R_3$ is —$CH_3$ or —$CH_2CH_3$, and
$R_4$ is H; —$CH_3$; —$CH_2CH_3$; —$OCH_3$ or —$OCH_2CH_3$, and
$R_5$ is H; —$CH_3$; —$CH_2CH_3$; —$OCH_3$ or —$OCH_2CH_3$, and
or $R_4$ and $R_5$ form a $C_4$-$C_8$ ring system, which can be aliphatic or aromatic, and
$R_6$ is H; —$CH_3$; —$CH_2CH_3$; —$OCH_3$ or —$OCH_2CH_3$, and
$R_7$ is H; —$CH_3$; —$CH_2CH_3$; —$OCH_3$ or —$OCH_2CH_3$, and
$R_8$ is H; —$CH_3$ or —$CH_2CH_3$, and
$R_9$ is —$CH_3$ or —$CH_2CH_3$, and
m is 0, 1 or 2, and
n is 0, 1 or 2,
with the proviso that the sum of m+n is 1 or 2,
o is 2 or 3,
a is 0, 1, 2, or 3,
b is 0, 1, 2, or 3,
with the proviso that the sum of a+b is 2 or 3.

Therefore the present invention also relates to a catalyst (C") of formula (III)

$$[M(L)(X)_a(L')_b],$$ (III)

wherein
M is a transition metal chosen from the group consisting of Ru and Fe, and
X is a halogen anion (preferably Cl⁻), and
L' is triphenylphosphine, and
L is a tridentate ligand of formula (IV)

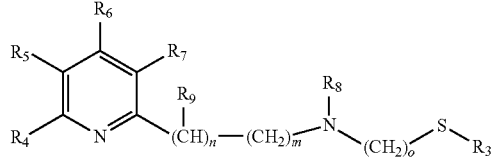

(IV)

wherein
$R_3$ is —$CH_3$ or —$CH_2CH_3$, and
$R_4$ is H; —$CH_3$; —$CH_2CH_3$; —$OCH_3$ or —$OCH_2CH_3$, and
$R_5$ is H or —$CH_3$, and
or $R_4$ and $R_5$ form a $C_4$-$C_8$ ring system, which can be aliphatic or aromatic, and
$R_6$ is H or —$CH_3$, and
$R_7$ is H or —$CH_3$, and
$R_8$ is H or —$CH_3$, and
$R_9$ is —$CH_3$, and
m is 0 or 1, and
n is 0 or 1,
with the proviso that the sum of m+n is 1,
o is 2,
a is 1 or 2,
b is 1 or 2,
with the proviso that the sum of a+b is 3.

Therefore the present invention also relates to a catalyst (C''') of formula (III')

$$M(L)(X)_2(L'),$$ (III')

wherein
M is Ru or Fe, and
X is Cl⁻, and
L' is PPh₃, and
L is a tridentate ligand chosen from the group consisting of the ligands of formulae (IVa)-(IVl)

(IVa)

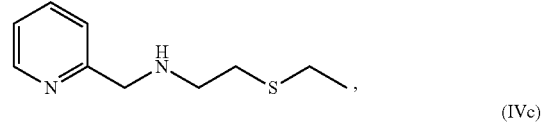
(IVb)

(IVc)

(IVd)

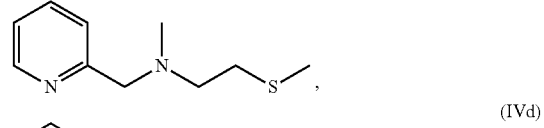
(IVe)

(IVf)

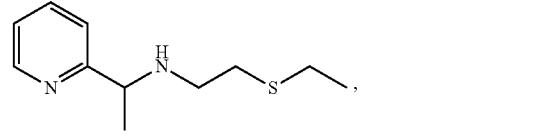
(IVg)

(IVh)

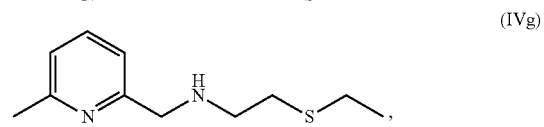
(IVi)

(IVj)

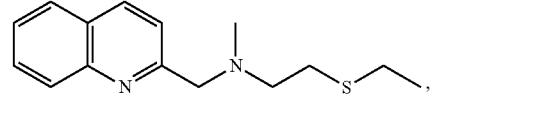

-continued (IVk)

[Structure: pyridine with methoxy group, -CH2-NH-CH2CH2-S-CH2CH3], and (IVl)

[Structure: quinoline-CH2-NH-CH2CH2-S-CH2CH3],

In the following the synthesis of the catalyst used in the selective reduction of the present invention is described.
Production of the Ligand L (Compounds of Formula (IV)

The ligand (L) is usually made first and this ligand (L) is then used afterwards to synthesise the transition metal based catalyst of formula (III).

The production of the ligands (wherein $R_8$ is H) is usually done by the following reaction scheme (RS):

[Reaction scheme showing compound (V): pyridine with $R_4, R_5, R_6, R_7$ substituents and $C(=O)R_{10}$ group + compound (VI): $H_2N-(CH_2)_o-S-R_3$ → compound (IV'): pyridine with $R_4, R_5, R_6, R_7$ and $C(R_{10})=N-(CH_2)_o-S-R_3$ → compound (IV''): pyridine with $R_4, R_5, R_6, R_7$ and $-(CH)_n-(CH_2)_m-NH-(CH_2)_o-S-R_3$ with $R_9$ substituent]

(V), (VI), (IV'), (IV'')

wherein $R_{10}$ is H or has the same meaning as $R_9$, all other substituents and o have the meanings as defined above.

To obtain the ligands (wherein $R_8$ is $-CH_3$ or $-CH_2CH_3$), the process of RS is carried out and then in an additional step the amino group is alkylated.

The process of the production of the ligand is usually carried out in a solvent (or a mixture of solvents).

Suitable solvents are esters, ethers, amides, hydrocarbons, halogenated hydrocarbons and alcohols. Preferred solvents are $CH_2Cl_2$, toluene, ethyl acetate, THF, methanol and ethanol.

The process of the production of the ligand is usually carried out at temperature of between 0 and 120° C. (preferably 0-40° C.).

The process of the production of the ligand is usually carried at ambient pressure.

The obtained ligand of formula (IV'') (with $R_8$=H) is removed from the reaction mixture by extraction and can be further purified if required. The yield is very good.

To obtain the ligands of formula (IV) wherein $R_8$ is $-CH_3$ or $-CH_2CH_3$, the obtained ligand of formula (IV'') is alkylated in an additional step.

This alkylation step can be carried out according to commonly known processes.
Production of the Catalyst (Compounds of Formula (III))

As stated above the catalysts of the present invention are new.

They are produced by commonly known processes. Usually (and preferably in the context of the present invention) they are produced as follows (reaction scheme (RS2)):

[Reaction scheme showing compound (IV): pyridine with $R_4, R_5, R_6, R_7$ substituents and $-(CH_2)_m-(CH)_n-N(R_8)(R_9)$-... $(CH_2)_o-S-R_3$ + $M(X)_2(L')_q$ (VII)]

(IV), (VII)

wherein q is 1, 2 or 3 and
all other substituents have the meanings as defined above.

The process to obtain the catalyst (RS2) is usually carried out in a solvent (or a mixture of solvents). Suitable solvents are esters, ethers, amides, hydrocarbons, and alcohols. Preferred solvents are toluene, ethyl acetate, THF and diglyme.

The process to obtain the catalyst is usually carried out at elevated temperature (50-180°).

The process to obtain the catalyst is usually carried out at ambient pressure.

The obtained catalyst (in crystalline form) are filtered off and they can be further purified.

As stated above the obtained catalysts are used in the selective reductions (selective hydrogenations), wherein the yield and selectivity of the desired product is excellent.
Reduction Process The reduction process (selective hydrogenation) of the compound of formula (I) can be carried out according to the following reaction scheme

[Reaction scheme: compound (I) with $R_1, R_2, R$ and C=O → compound (IIa) with $R_1, R_2, R$ and OH, using $H_2$ and catalyst of formula (III)]

(I), (IIa)

wherein all substituents have meanings as defined above.

In these hydrogenation processes $H_2$ is added in form of a gas (pure $H_2$ gas or a mixture).

The catalyst of formula (III) according to the present invention is usually used in an amount of 0.001-0.5 mol-% (based on the number of moles of the compounds of formula (I)).

Therefore, the present invention also relates to a process (P7), which is process (P), (P1), (P1'), (P1"), (P1'''), (P1''''), (P2), (P2'), (P2"), (P3), (P3'), (P4), (P5), (P5') or (P6), wherein the at least one catalyst of formula (III) is used in an amount of 0.001-0.5 mol-% (based on the number of moles of the compounds of formula (I)).

The hydrogenation process can be carried out with (pure) $H_2$ gas or with a gas which comprises $H_2$. Preferably the hydrogenation process according to the present invention is carried out with (pure) $H_2$ gas.

Therefore, the present invention also relates to a process (P8), which is process (P), (P1), (P1'), (P1"), (P1'''), (P1''''), (P2), (P2'), (P2"), (P3), (P3'), (P4), (P5), (P5'), (P6) or (P7), wherein the hydrogenation is carried out with (pure) $H_2$ gas or with a gas which comprises $H_2$ (preferably with (pure) $H_2$ gas).

The hydrogenation process can be carried out at ambient pressure as well as at elevated pressure. Preferably the hydrogenation process according to the present invention is carried out at elevated pressure (10-50 bar), usually in an autoclave (or any other vessel, which can resist the pressure.

Therefore, the present invention also relates to a process (P9), which is process (P), (P1), (P1'), (P1"), (P1'''), (P1''''), (P2), (P2'), (P2") (P3), (P3'), (P4), (P5), (P5'), (P6), (P7) or (P8), wherein the hydrogenation is carried out at ambient pressure.

Therefore, the present invention also relates to a process (P10), which is process (P), (P1), (P1'), (P1"), (P1'''), (P1''''), (P2), (P2'), (P2") (P3), (P3'), (P4), (P5), (P5'), (P6), (P7) or (P8), wherein the hydrogenation is carried out at out at elevated pressure (10-50 bar).

The hydrogenation can be carried out in a solvent (or mixture of solvents). Suitable solvents are esters, ethers, amides, hydrocarbons, halogenated hydrocarbons and alcohols. Preferred solvents are $CH_2Cl_2$, toluene, ethyl acetate, THF, methanol, ethanol and isopropanol, especially preferred solvents are toluene and isopropanol.

Therefore, the present invention also relates to a process (P11), which is process (P), (P1), (P1'), (P1"), (P1'''), (P1''''), (P2), (P2'), (P2") (P3), (P3'), (P4), (P5), (P5'), (P6), (P7), (P8), (P9) or (P10), wherein the hydrogenation is carried out in at least one a solvent.

Therefore, the present invention also relates to a process (P11'), which is process (P11), wherein the hydrogenation is carried out in at least one a solvent chosen from the group consisting of esters, ethers, amides, hydrocarbons, halogenated hydrocarbons and alcohols. Preferred solvents are $CH_2Cl_2$, toluene, ethyl acetate, THF, methanol, ethanol and isopropanol, especially preferred solvents are toluene and isopropanol.

Therefore, the present invention also relates to a process (P11"), which is process (P11), wherein the hydrogenation is carried out in at least one a solvent chosen from the group consisting of $CH_2Cl_2$, toluene, ethyl acetate, THF, methanol, ethanol and isopropanol (especially preferred are toluene and isopropanol).

The hydrogenation is usually carried out at an elevated temperature (30-150° C.).

Therefore, the present invention also relates to a process (P12), which is process (P), (P1), (P1'), (P1"), (P1'''), (P1''''), (P2), (P2'), (P2") (P3), (P3'), (P4), (P5), (P5'), (P6), (P7), (P8), (P9), (P10), (P11), (P11') or (P11"), wherein the hydrogenation is carried out at an elevated temperature (30-150° C.).

It is also possible to reduce the compound of formula (I) selectively by a transfer hydrogenation process. In that case no $H_2$ gas needs to be added. As reductant any suitable hydrogen donor can be used, including secondary alcohols, such as isopropanol and formic acid, its salts or derivatives.

Therefore the present invention also relates to a process (P13), which is process (P), (P1), (P1'), (P1"), (P1'''), (P1''''), (P2), (P2'), (P2") (P3), (P3'), (P4), (P5), (P5'), (P6) or (P7), wherein the reduction is a transfer hydrogenation.

The following examples serve to illustrate the invention. If not otherwise stated the temperature is given in ° C.

EXAMPLES

General:

Transition metal precursors, reagent and solvents were obtained from commercial sources and used as received unless noted otherwise. GC analysis was carried out on an Agilent 7890B GC system with a HP-5 normal-phase silica column, using Helium as a carrier gas and dodecane as an internal standard. NMR spectra were recorded on a Bruker AV400, Bruker AV300 or Bruker Fourier300 NMR spectrometer. $^1H$ and $^{13}C$-NMR spectra were referenced w.r.t. the solvent signal. Chemical shifts are in ppm, coupling constants in Hz. HR-MS measurements were recorded on an Agilent 6210 Time-of-Flight LC/MS, peaks as listed correspond to the highest abundant peak and are of the expected isotope pattern.

Ligand Synthesis

Example 1: 2-(ethylthio)-N-((6-methylpyridin-2-yl)methyl)ethan-1-amine [ligand of Formula (IVg)]

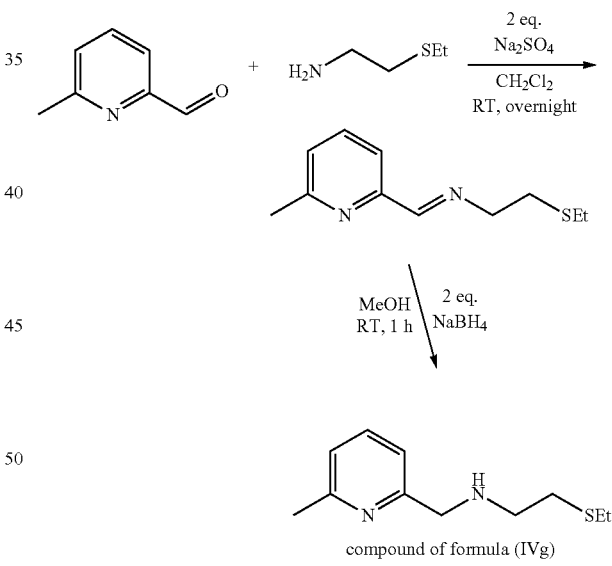

compound of formula (IVg)

6-methylpyridine-2-carboxaldehyde (3.0 g, 25 mmol) and 2-(Ethylthio)ethylamine (2.63 g, 2.8 mL, 25 mmol) were dissolved in $CH_2Cl_2$ (75 mL), then $Na_2SO_4$ (7.1 g, 50 mmol) was added. The suspension was stirred at room temperature overnight, filtered and the filter cake was washed with $CH_2Cl_2$. The combined volatiles were removed in vacuo, yielding 5.45 g of imine as brown oil, which was used directly in the following step without further purification. Therefore, the imine was dissolved in MeOH (50 mL) and $NaBH_4$ (1.9 g, 51 mmol) was added portionwise at 0° C. The mixture was stirred at room temperature for another hour, after which the solvent was removed in vacuo. Then $CH_2Cl_2$ (20 mL) and water (20 mL) were added. The aqueous layer was extracted with $CH_2Cl_2$ (three times 20 mL). The combined organic layers were washed with brine (20 mL) and dried over $Na_2SO_4$. Evaporating the solvent and drying in vacuo yielded 4.95 g (94%) of the ligand of formula (IVg) as an orange oil, which was directly used for complex synthesis.

$^1$H-NMR (300 MHz, $CDCl_3$): δ 7.45 (t, 1H, J=7.6, $CH_{arom}$), 7.07 (d, 1H, J=7.8, $CH_{arom}$), 6.96 (d, 1H, J=7.5, $CH_{arom}$), 3.84 (s, 2H), 2.80 (dt, 2H), 2.66 (dt, 2H), 2.48 (m, 5H), 1.23 (t, 3H, J=7.4) ppm. $^{13}$C-NMR (75 MHz, $CDCl_3$): δ 158.9, 157.8, 136.5, 121.3, 118.9, 54.9, 48.2, 31.8, 25.6, 24.4 ppm.

HRMS (ESI+): calculated for $C_{11}H_{18}N_2S$: 210.1191; found 211.1265 (M+H), 233.1082 (M+Na).

Example 2: 2-(methylthio)-N-((pyridin-2-yl)methyl)ethan-1-amine [ligand of Formula (IVa)]

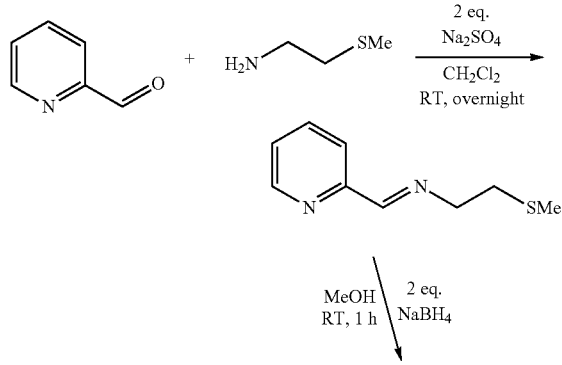

compound of formula (IVa)

The ligand of formula (IVa) was prepared in analogy to Example 1.

$^1$H NMR (300 MHz, $CD_2Cl_2$) δ 8.43 (ddd, 1H, J=4.9 Hz, J=1.8 Hz, J=0.9 Hz, $CH_{arom}$), 7.57 (td, 1H, J=7.7 Hz, J=1.8 Hz, $CH_{arom}$), 7.24 (d, 1H, J=7.8 Hz, $CH_{arom}$), 7.07 (dd, 1H, J=7.5 Hz, J=5.0.7 Hz, $CH_{arom}$), 3.81 (s, 2H), 2.75 (td, 2H, J=6.5 Hz, J=0.8 Hz, $CH_2$), 2.58 (td, 2H, J=6.5 Hz, J=0.6 Hz, $CH_2$), 1.99 (s, 3H, $CH_3$) ppm.

$^{13}$C NMR (75 MHz, $CD_2Cl_2$): δ 160.2, 149.1, 136.2, 121.9, 121.7, 54.8, 47.6, 34.4, 15.0 ppm.

HRMS (ESI+): calculated for $C_9H_{14}N_2S$: 182.0878 (M+H): 183.0950; found 183.0950 (M+H).

Example 3: 2-(ethylthio)-N-((pyridin-2-yl)methyl)ethan-1-amine [ligand of Formula (IVb)]

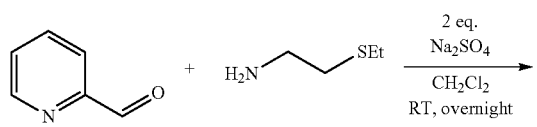

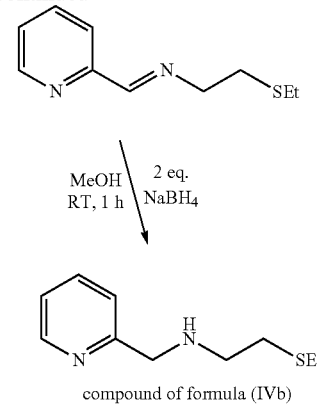

compound of formula (IVb)

The ligand of formula (IVb) was prepared according to Example 1.

$^1$H NMR (300 MHz, $CD_2Cl_2$): δ 8.51 (ddd, 1H, J=4.8 Hz, J=1.5 Hz, J=0.9 Hz, $CH_{arom}$), 7.64 (td, 1H, J=7.5 Hz, J=1.8 Hz, $CH_{arom}$), 7.32 (d, 1H, J=7.8 Hz, $CH_{arom}$), 7.19-7.12 (m, 1H, $CH_{arom}$), 3.88 (s, 2H, $CH_2$), 2.85-2.79 (m, 2H, $CH_2$), 2.72-2.66 (m, 2H, $CH_2$), 2.52 (q, 2H, J=7.5 Hz, $CH_2$), 2.09 (d, 1H, J=9.6 Hz, NH), 1.23 (t, 3H, J=7.4 Hz, $CH_3$) ppm.

$^{13}$C NMR (75 MHz, $CD_2Cl_2$): δ 161.6, 149.7, 136.8, 122.5, 122.3, 55.4, 48.9, 32.5, 26.2, 15.3 ppm.

HRMS (ESI+): calculated for $C_{10}H_{16}N_2S$: 196.1034; (M+H): 197.1107; (M+Na): 219.0926; found 197.1108 (M+H), 219.0929 (M+Na).

Example 4: 2-(ethylthio)-N-((6-methoxy-pyridin-2-yl)methyl)ethan-1-amine [ligand of Formula (IVk)]

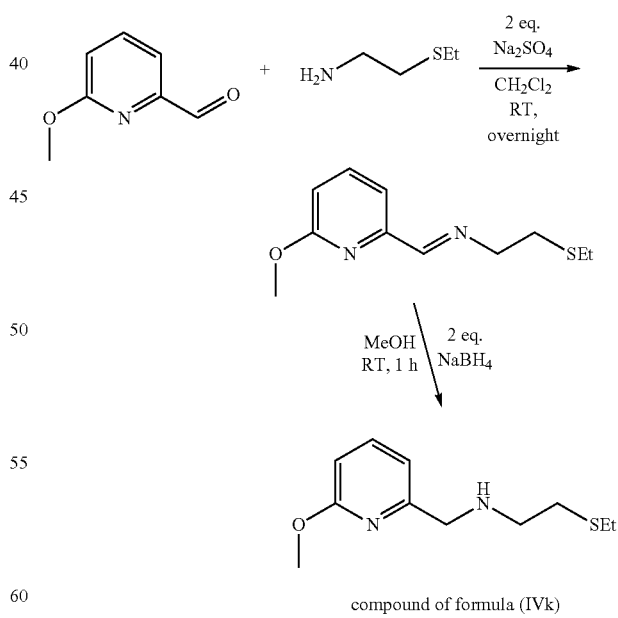

compound of formula (IVk)

The ligand of formula (IVk) was prepared according to Example 1 in a 84% yield. $^1$H-NMR (300 MHz, $CDCl_3$): δ 7.54 (dd, 1H, J=8.1, J=7.4, $CH_{arom}$), 6.87 (d, 1H, J=7.2), 6.63 (d, 1H, J=8.1), 4.55 (s, NH), 3.92 (s, 3H), 3.90 (m, NH), 3.80 (s, 2H), 2.83 (t, 2H, J=6.5), 2.66 (t, 2H, J=6.5), 2.52 (t, 2H, J=7.5), 1.23 (t, 3H, J=7.2) ppm. $^{13}$C-NMR (75 MHz, CDCl$_3$): δ 163.8, 157.3, 138.8, 114.5, 108.7, 54.3, 53.2, 48.1, 32.0, 25.8, 14.8 ppm.

HRMS (ESI+): calculated for C$_{11}$H$_{18}$N$_2$OS: 227.1213 (M+H); found 227.1217 (M+H), 227.1217 (M+Na).

Example 5: 2-(ethylthio)-N-((quinolin-2-yl)methyl)ethan-1-amine [ligand of Formula (IVl)]

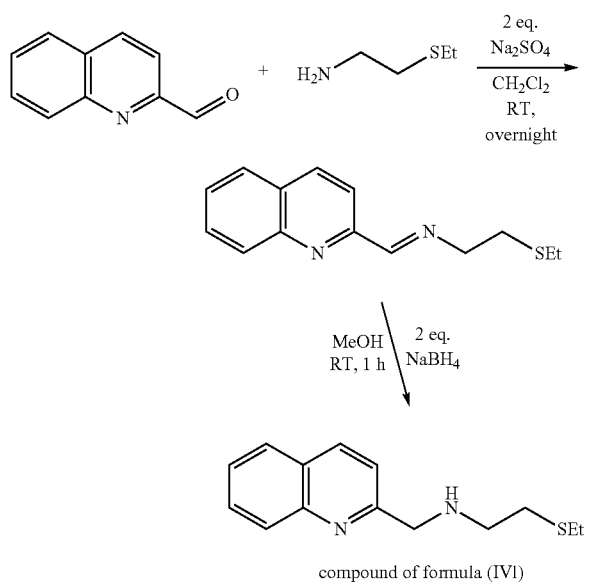

compound of formula (IVl)

The ligand of formula (IVl) was prepared according to Example 1 and purification by Kugelrohr distillation.

$^1$H NMR (300 MHz, CD$_2$Cl$_2$): δ 8.13 (d, 1H, J=8.4 Hz, CH$_{arom}$), 8.00 (d, 1H, J=8.7 Hz, CH$_{arom}$), 7.82 (dd, 1H, J=8.3 Hz, J=1.5 Hz, CH$_{arom}$), 7.69 (ddd, 3H, J=8.5 Hz, J=6.9 Hz, J=1.5 Hz, CH$_{arom}$), 7.55-7.45 (m, 2H, CH$_{arom}$), 4.08 (s, 2H, CH$_2$), 2.89 (td, 2H, J=6.8 Hz, J=1.2 Hz, CH$_2$), 2.73 (td, 2H, J=6.4 Hz, J=0.9 Hz, CH$_2$), 2.55 (q, 2H, J=7.4 Hz, CH$_2$), 2.14 (d, 1H, J=11.4 Hz, NH), 1.24 (t, 3H, J=7.4 Hz, CH$_3$) ppm.

$^{13}$C NMR (75 MHz, CD$_2$Cl$_2$): δ 161.5, 136.7, 129.8, 129.5, 128.1, 127.9, 126.5, 121.0, 56.0, 49.1, 32.6, 26.2, 15.29 ppm.

HRMS (ESI+): calculated for C$_{14}$H$_{18}$N$_2$S: 246.1191; (M+H): 247.1264; found 247.1267 (M+H).

Example 6: 2-(ethylthio)-N-(1-(pyridin-2-yl)ethyl)ethan-1-amine [ligand of Formula (IVe)]

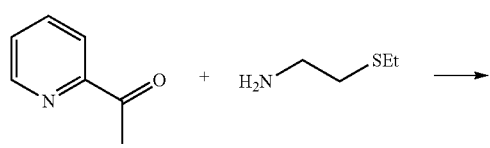

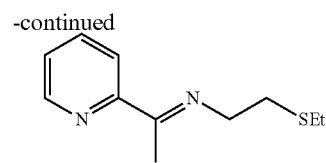

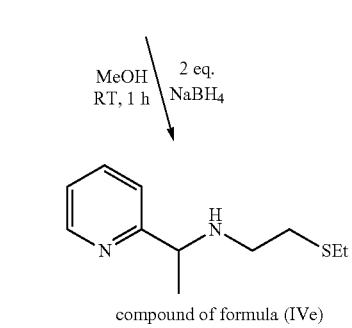

compound of formula (IVe)

The ligand of formula (IVe) was prepared according to Example 1 with imine formation performed in the presence of 5 mol % of p-toluenesulfonic acid in toluene under reflux conditions and purification by Kugelrohr distillation.

$^1$H NMR (300 MHz, CD$_2$Cl$_2$): δ 8.51 (ddd, 1H, J=4.8 Hz, J=1.9 Hz, J=1.0 Hz, CH$_{arom}$), 7.64 (td, 1H, J=7.6 Hz, J=1.8 Hz, CH$_{arom}$), 7.32 (dt, 1H, J=7.8 Hz, J=1.1 Hz, CH$_{arom}$), 7.14 (ddt, 1H, J=7.5 Hz, J=4.8 Hz, J=1.2 Hz, CH$_{arom}$), 3.84 (q, 1H, J=6.9 Hz, CH), 2.71-2.55 (m, 4H, CH$_2$), 2.47 (q, 2H, J=7.4 Hz, CH$_2$), 2.05 (d, 1H, J=39.3 Hz, NH), 1.34 (d, 3H, J=6.9 Hz, CH$_3$), 1.20 (d, 3H, J=7.5 Hz, CH$_3$) ppm. $^{13}$C NMR (75 MHz, CD$_2$Cl$_2$): δ 165.4, 149.7, 136.9, 122.3, 121.4, 59.7, 47.1, 32.7, 26.1, 23.2, 15.2 ppm.

HRMS (ESI+): calculated for C$_{11}$H$_{18}$N$_2$S: 210.1191; (M+H), 211.1264; (M+Na): 233.1083; found 211.1265 (M+H), 233.1083 (M+Na).

Example 7: 2-(ethylthio)-N-methyl-N-(pyridin-2-ylmethyl)ethan-1-amine [ligand of Formula (IVd)]

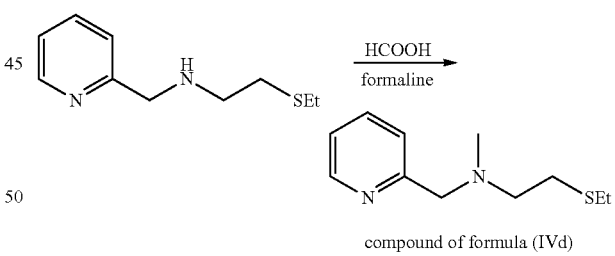

compound of formula (IVd)

2-(Ethylthio)-N-(pyridin-2-ylmethyl)ethan-1-amine (ligand of formula (IVb), 850 mg, 3.75 mmol), formalin (4 mL of 37% wt formaldehyde in water) and formic acid (4 mL) were stirred at 70° C. overnight. All volatiles were removed in vacuo and CH$_2$Cl$_2$ (10 mL) and saturated NaHCO$_3$ solution (10 mL) were added. The aqueous layer was extracted with CH$_2$Cl$_2$ (three times 10 mL). The combined organic layers were washed with brine (20 mL) and dried over Na$_2$SO$_4$. Removal of the solvent yielded 754 mg (3.59 mmol, 96%) of 2-(ethylthio)-N-methyl-N-(pyridin-2-ylmethyl)ethan-1-amine as an orange liquid (ρ=1.081 g cm$^{-3}$). The ligand of formula (IVb) was further purified by Kugelrohr distillation.

¹H-NMR (300 MHz, CDCl₃): δ 8.46 (d, 1H, J=5.1, CH$_{arom}$), 7.58 (dt, 1H, J=7.8, J=1.8, CH$_{arom}$), 7.38 (d, 1H, J=7.8, CH$_{arom}$), 7.08 (ddd, 1H, J=7.5, J=4.8, J=1.2, CH$_{arom}$), 3.62 (S, 2H), 2.62 (S, 4H), 2.45 (q, 2H, J=7.4), 2.31 (s, 3H, N—CH₃), 1.17 (t, 3H, J=7.4) ppm.

¹³C NMR (101 MHz, CDCl₃): δ 159.2, 149.0, 136.4, 123.1, 122.0, 63.6, 57.3, 56.9, 42.4, 31.9, 29.3, 26.1, 14.8 ppm.

HRMS (ESI+): calculated for C₁₁H₁₈N₂S: 210.1191; found 211.1265 (M+H), 233.1084 (M+Na).

Catalyst Synthesis

Example 8: Ru(6-MeNNS$^{Et}$)(PPh₃)Cl₂

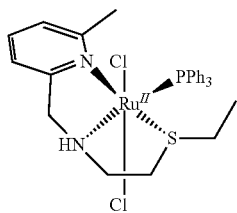

RuCl₂(PPh₃)₃ (1 g, 1.04 mmol) and the ligand of formula (IVg) (obtained from Example 1) (231.4 mg, 1.1 mmol) were placed in a 25 mL Schlenk tube under argon atmosphere, and dissolved in dry diglyme (2 mL). The reaction mixture was heated to 165° C. for 2 h, allowed to cool down to room temperature and stored at −18° C. to precipitate further overnight. Cold Et₂O (2 mL) was added while cooling with a dry ice/iso-propanol bath. The precipitate was filtrated by cannula, and washed with Et₂O (5 times 2 mL). The orange powder was dried in vacuo, affording 530 mg (79%) of Ru(6-MeNNS$^{Et}$)(PPh₃)Cl₂ as an orange powder. An equilibrium of two conformations of Ru(6-MeNNS$^{Et}$)(PPh₃)Cl₂ are existent in solution, delivering a doubled set of signals in NMR. For ¹H-NMR only data of the major conformation is given due to overlapping signals.

¹H-NMR (300 MHz, CD₂Cl₂): δ 7.67-7.16 (m, 17H, CH$_{arom}$), 7.01 (d, 1H, J=7.8, CH$_{arom}$), 5.65 (m, 2H), 4.47 (m, 1H), 3.5 (m, 1H), 3.34 (m, 1H), 3.22 (d, 1H, J=11.1), 2.98 (m, 1H), 2.59 (m, 1H), 1.53 (m, 2H), 0.87 (t, 3H, J=7.5) ppm.

³¹P-NMR (122 MHz, CD₂Cl₂): δ 48.8, 45.8 ppm.

HRMS (ESI+): calculated for C₂₉H₃₂Cl₂N₂PRuS (M+H): 644.0518; found 644.0518 (M+H), 667.0412 (M+Na).

Example 9: Ru(NNS$^{Me}$)(PPh₃)Cl₂

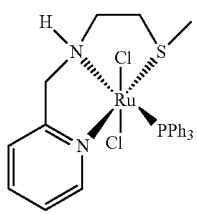

Ru(NNS$^{Me}$)(PPh₃)Cl₂ was prepared according to Example 8. An equilibrium of two conformations was obtained.

¹H-NMR (300 MHz, CD₂Cl₂): δ 8.47 (d, 1H, J=5.7), 7.72 (m, 1H), 7.56 (m, 6H), 7.32 (m, 10H), 6.86 (t, 1H, J=6.3), 5.45 (s, broad, 1H, NH), 5.20 (t, 1H, J=12.6), 4.38 (m, 1H), 3.41 (m, 2H), 3.26 (d, 1H, J=11.1), 2.55 (m, 1H), 1.50 (s, 3H).

³¹P-NMR (122 MHz, CD₂Cl₂): δ 51.8, 50.7

HRMS (ESI+): calculated for C₂₇H₂₉C₁₂N₂PRuS: 616.0210 (M+); found 616.0197 (M+).

Example 10: Ru(NNS$^{Et}$)(PPh₃)Cl₂

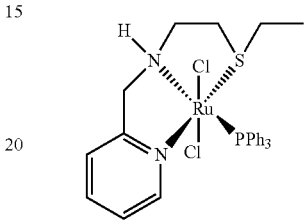

Ru(NNS$^{Et}$)(PPh₃)Cl₂ was prepared according to Example 8. An equilibrium of two conformations was obtained in 84% yield.

¹H-NMR (300 MHz, CD₂Cl₂): δ 8.45 (d, 1H, J=5.7), 7.72 (m, 1H), 7.57 (m, 6H), 7.34 (m, 10H), 6.86 (t, 1H, J=6.3), 5.49 (s, broad, 1H, NH), 5.22 (t, 1H, J=13.5), 4.40 (m, 1H), 3.47 (m, 2H), 3.36 (m, 1H), 2.80 (m, 1H), 2.52 (m, 1H), 1.27 (m, 2H), 1.19 (m, 1H), 0.95 (t, 3H, J=7.5)

³¹P-NMR (122 MHz, CD₂Cl₂): δ 51.8, 50.7

HRMS (ESI+): calculated for C₂₈H₃₁C₁₂N₂PRuS: 630.0366 (M+); found 630.0388 (M+), 653.0270 (M+Na).

Example 11: Ru(6-MeONNS$^{Et}$) (PPh₃)Cl₂

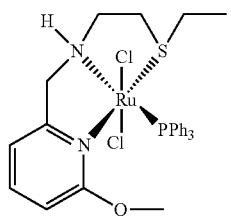

Ru(6-MeONNS$^{Et}$)(PPh₃)Cl₂ was prepared according to Example 8. An equilibrium of two conformations was obtained in 88% yield.

¹H-NMR (400 MHz, CD₂Cl₂): δ 7.94 (m, 2H), 7.65 (m, 2H), 7.42-7.14 (m, 12H), 7.07 (d, 1H, J=7.6), 6.56 (d, 1H, J=8.4), 5.56-5.36 (m, 2H), 4.46 (m, 1H), 3.50-3.19 (m, 2H), 3.21 (dd, 1H, J=11.0, J=2.2), 2.87 (m, 1H), 2.83 (s, 3H, twinned), 2.50 (m, 1H), 1.33 (m, 1H), 0.87 (t, 3H, twinned, overlapping)

³¹P-NMR (122 MHz, CD₂Cl₂): δ 47.2, 45.9

HRMS (ESI+): calculated for C₂₉H₃₂C₁₂N₂OPRuS (M+H): 660.0468; found: 660.0469 (M+H), 683.0363 (M+Na).

Example 12: Ru(QuinNS$^{Et}$) (PPh$_3$)Cl$_2$

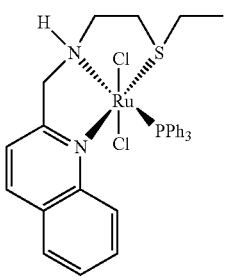

Ru(QuinNS$^{Et}$)(PPh$_3$)Cl$_2$ was prepared according to Example 8. An equilibrium of two conformations was obtained.

$^1$H-NMR (300 MHz, CD$_2$Cl$_2$): δ 8.12 (d, 2H, J=8.4), 7.74-6.66 (m, 19H), 5.90 (s, broad, NH), 5.74 (t, 1H, J=13.3), 4.72 (m, 1H), 3.58-3.40 (m, 3H), 3.05 (m, 1H), 2.72 (m, 1H), 1.66 (m, 1H), 0.95 (t, 3H, J=7.5)

$^{31}$P NMR (122 MHz, CD$_2$Cl$_2$): δ 48.90, 45.86

HRMS (ESI+): calcd. for C$_{32}$H$_{33}$Cl$_2$N$_2$PRuS: 680.0519 (M+); found 680.0500 (M+).

Example 13: Ru(N-Me-NS$^{Et}$) (PPh$_3$)Cl$_2$

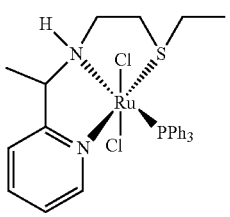

Ru(N-Me-NS$^{Et}$)(PPh$_3$)Cl$_2$ was prepared according to Example 8. An equilibrium of two conformations was obtained.

$^1$H-NMR (300 MHz, CD$_2$Cl$_2$): δ 8.53 (d, 1H, J=5.7), 7.72 (m, 1H), 7.57 (m, 6H), 7.33 (m, 10H), 6.85 (t, 1H, J=6.6), 5.35 (m, 1H), 4.93 (s, broad, NH), 3.68-3.31 (m, 3H), 2.81 (m, 1H), 2.53 (m, 1H), 1.80 (d, 3H, J=6.9), 1.25 (m, 1H), 0.97 (t, 3H, J=7.2)

$^{31}$P NMR (122 MHz, CD$_2$Cl$_2$): δ 51.5, 50.3

HRMS (ESI+): calculated for C$_{29}$H$_{33}$Cl$_2$N$_2$PRuS: 644.0518 (M+); found 644.0513 (M+).

Example 14: Ru(NN$^{Me}$S$^{Et}$)(PPh$_3$)Cl$_2$

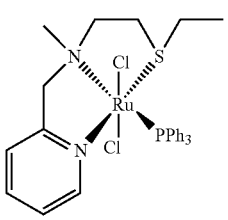

Ru(NN$^{Me}$S$^{Et}$)(PPh$_3$)Cl$_2$ was prepared according to Example 8. An equilibrium of two conformations was obtained in 54%.

$^1$H-NMR (300 MHz, CD$_2$Cl$_2$): δ 8.11 (d, 1H, J=5.7), 7.92 (m, 6H), 7.47 (dt, 1H, J=7.5, J=1.5), 7.30 (m, 10H), 6.56 (t, 1H, J=7.5), 5.67 (d, 1H, J=14.4), 3.87 (d, 1H, J=14.4), 3.15 (s, 3H), 2.86 (m, 1H), 2.70 (m, 1H), 2.30 (m, 2H), 0.74 (m, 1H), 0.67 (t, 3H, J=6.9), 0.42 (m, 1H)

$^{31}$P-NMR (122 MHz, CD$_2$Cl$_2$): δ 51.4, 50.4

HRMS (ESI+): calculated for C$_{29}$H$_{33}$Cl$_2$N$_2$PRuS: 644.0518 (M+); found 644.0505 (M+).

Hydrogenation Reactions

Example 15: Selective Hydrogenation of Cinnamaldehyde

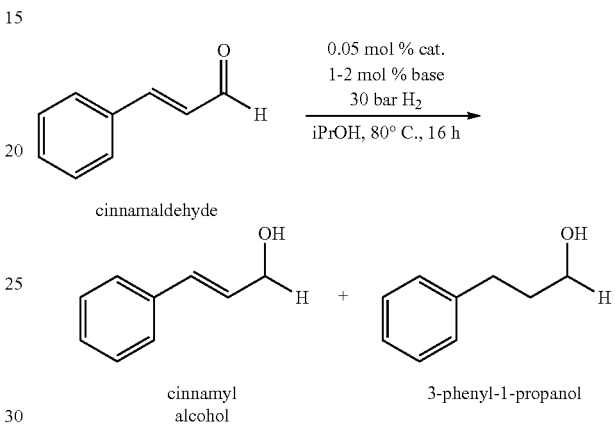

4 mL glass reaction vials and stirring bars were dried overnight at 110° C. The reaction vessels were charged with LiOtBu (1 mg, 0.0125 mmol, 1.25 mol %), closed with PTFE/rubber septa, placed in a multiple reactor inlet suitable for a pressure vessel, and brought under argon atmosphere by three vacuum-argon cycles. With a syringe Ru(NNS$^{Et}$)(PPh$_3$)Cl$_2$ (catalyst of Example 10) was added as stock solution in iPrOH (1 mL, 0.0005 mol/L, 0.05 mol %), followed by a solution of cinnamaldehyde in iPrOH (1 mL, 1 mol/L, 1 mmol). The reaction mixtures were transferred to an argon-filled pressure vessel, which was immediately flushed with three nitrogen and three hydrogen cycles, then pressurized to 30 bar hydrogen, heated to 80° C. and stirred for 16 h. After that, the pressure vessel was allowed to cool down to room temperature and depressurized. The reaction mixtures were filtered over silica and rinsed with ethanol (2 mL) after which dodecane was added as an internal standard prior to GC analysis. The products are determined based on GC analysis retention time. The given values for conversion (C), yield (Y), and selectivity (S) [%] are mol % with regard to the initial cinnamaldehyde amount, and corrected by dodecane.

The results are summarized in Table 1

The same conditions were chosen for the hydrogenation wherein the catalyst of example 9 (Ru(NNS$^{Me}$)(PPh$_3$)Cl$_2$ was used. These results are summarized in Table 2

TABLE 1

| Exp | Base 1-2 mol % | Conversion C [%] | Cinnamyl-alcohol Y [%] | | 3-phenyl-1-propanol Y [%] | |
|---|---|---|---|---|---|---|
| | | | | S [%] | | S [%] |
| 15a | — | 19 | 0 | 0 | 0 | 0 |
| 15b | LiOtBu | 96 | 72 | 75 | 4 | 4 |

TABLE 1-continued

| | Base | Conversion | Cinnamyl-alcohol | | 3-phenyl-1-propanol | |
|---|---|---|---|---|---|---|
| Exp | 1-2 mol % | C [%] | Y [%] | S [%] | Y [%] | S [%] |
| 15c | KOtBu | 99 | 84 | 85 | 5 | 5 |
| 15d | CaCO₃ | 16 | 2 | 13 | 0 | 0 |
| 15e | Na(COOPh) | 15 | 0 | 0 | 0 | 0 |

TABLE 2

| | Base | Conversion | Cinnamyl-alcohol | | 3-phenyl-1-propanol | |
|---|---|---|---|---|---|---|
| Exp | 1-2 mol % | C [%] | Y [%] | S [%] | Y [%] | S [%] |
| 15f | — | 19 | 0 | 0 | 0 | 0 |
| 15g | LiOtBu | >99 | 78 | 78 | 3 | 3 |
| 15h | KOtBu | >99 | 69 | 69 | 3 | 3 |
| 15i | K₂CO₃ | 52 | 23 | 43 | 0 | 0 |

Example 16

4 mL glass reaction vials and stirring bars were dried overnight at 110° C. The reaction vessels were charged with LiOtBu (1 mg, 0.0125 mmol, 1.25 mol %), closed with PTFE/rubber septa, placed in a multiple reactor inlet suitable for a pressure vessel, and brought under argon atmosphere by three vacuum-argon cycles. With a syringe the reaction vessels were charged with the catalyst as stock solution in iPrOH (1 mL, 0.0005 mol/L, 0.05 mol %), followed by a solution of cinnamaldehyde in iPrOH (1 mL, 1 mol/L). The reaction mixtures were transferred to an argon-filled pressure vessel, which was immediately flushed with three nitrogen and three hydrogen cycles, then pressurized to 30 bar hydrogen, heated to 80° C. and stirred for 16 h. After that, the pressure vessel was allowed to cool down to room temperature and depressurized. The reaction mixtures were filtered over silica and rinsed with ethanol (2 mL) after which dodecane was added as an internal standard prior to GC analysis. The products are determined based on GC analysis retention time. The given values for conversion (C), yield (Y), and selectivity (S) [%] are mol % with regard to the initial cinnamaldehyde amount, and corrected by dodecane.

Catalyst screening experiments with KOtBu were performed accordingly.

TABLE 3

| | Cat. 0.05 | Base 1-2 | Conversion | Cinnamyl-alcohol | | 3-phenyl-1-propanol | |
|---|---|---|---|---|---|---|---|
| Exp. | mol % | mol % | C [%] | Y [%] | S [%] | C [%] | Y [%] |
| 16a | Cat of Exp. 9 | LiOtBu | 100 | 77 | 77 | 3 | 3 |
| 16b | Cat of Exp. 9 | KOfBu | 100 | 75 | 75 | 4 | 4 |
| 16c | Cat of Exp. 10 | LiOtBu | 100 | 69 | 69 | 8 | 8 |
| 16d | Cat of Exp. 10 | KOtBu | 100 | 67 | 67 | 10 | 10 |
| 16e | Cat of Exp. 8 | KOtBu | 100 | 64 | 64 | 3 | 3 |
| 16f | Cat of Exp. 13 | LiOtBu | 100 | 65 | 65 | 0 | 0 |
| 16g | Cat of Exp. 13 | KOtBu | 100 | 74 | 74 | 5 | 5 |
| 16hi | Cat of Exp. 14 | LiOtBu | 100 | 81 | 81 | 3 | 3 |
| 16i | Cat of Exp. 14 | KOtBu | 100 | 46 | 46 | 2 | 2 |

Example 17: Hydrogenation of Different Aldehydes/Ketones

The compounds of formulae (A), (B) and (C) were hydrogenated.

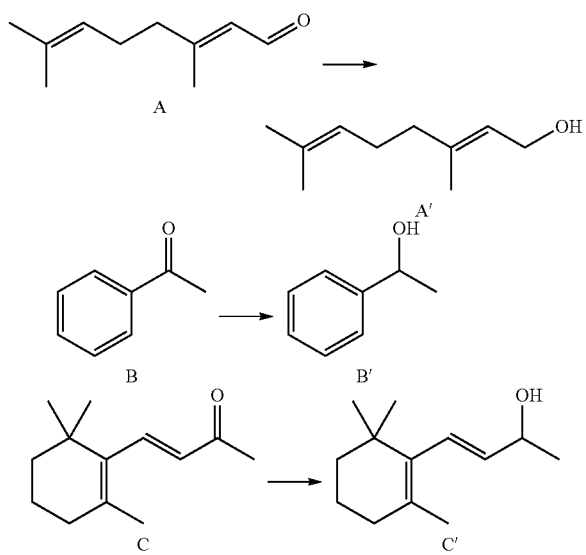

4 mL glass reaction vials and stirring bars were dried overnight at 110° C., closed with PTFE/rubber septa, placed in a multiple reactor inlet suitable for a pressure vessel, and brought under argon atmosphere by three vacuum-argon cycles. With a syringe the reaction vessels were charged with the catalyst as stock solution in iPrOH (1 mL, 0.0005 mol/L, 0.05 mol %), followed by a solution of the compound A, B or C in iPrOH (1 mL, 1 mol/L, 1 mmol). After that a solution of freshly sublimed the base in THF (12.5 μL, 1 mol/L, 0.0125 mmol, 1.25 mol %) was added with a Hamilton syringe. The reaction mixtures were transferred to an argon-filled pressure vessel, which was immediately flushed with three nitrogen and three hydrogen cycles, then pressurized to 30 bar hydrogen, heated to 80° C. and stirred for 16 h. After that the pressure vessel was cooled down to room temperature and depressurized. The reaction mixtures were filtered over silica and rinsed with ethanol (2 mL). The products are determined based on GC analysis retention time. The given values [%] are related to GC area %. The results are summarized in the following tables 4a, 4b and 4c.

TABLE 4a hydrogenation of the compound of formula (A)

| Cat. | Base | Conversion | Product Compund A' | |
|---|---|---|---|---|
| Exp. | 0.05 mol % | 1-2 mol % | C [%] | Y [%] | S [%] |
| 17a | Cat of Exp. 10 | KOtBu | 97 | 97 | 100 |

TABLE 4b hydrogenation of the compound of formula (B)

| Cat. | Base | Conversion | Product Compund B' | |
|---|---|---|---|---|
| Exp. | 0.05 mol % | 1-2 mol % | C [%] | Y [%] | S [%] |
| 17b | Cat of Exp. 9 | LiOtBu | 100 | 100 | 100 |
| 17c | Cat of Exp. 9 | KOtBu | 100 | 100 | 100 |
| 17d | Cat of Exp. 10 | LiOtBu | 100 | 100 | 100 |
| 17e | Cat of Exp. 10 | KOtBu | 100 | 100 | 100 |

TABLE 4c hydrogenation of the compound of formula (C)

| Cat. | Base | Conversion | Product Compund C' | |
|---|---|---|---|---|
| Exp. | 0.05 mol % | 1-2 mol % | C [%] | Y [%] | S [%] |
| 17f | Cat of Exp. 9 | LiOtBu | 99 | 96 | 96 |
| 17g | Cat of Exp. 9 | KOtBu | 100 | 96 | 96 |
| 17h | Cat of Exp. 10 | LiOtBu | 99 | 94 | 95 |
| 17i | Cat of Exp. 10 | KOtBu | 99 | 93 | 94 |

Example 18: Hydrogenation of Benzaldehyde

A 100 mL hastelloy autoclave with mechanical stirrer was charged with the catalyst of example 10 (3 mg, 0.005 mmol, 0.05 mol %), benzaldehyde (1.06 g, 10 mmol, 1.01 mL), 20 mL of isopropanol, and freshly sublimed KOtBu (14 mg, 0.125 mmol, 1.25 mol %) under an argon atmosphere. The autoclave vessel was flushed with nitrogen three times, pressurized to 30 bar $H_2$ and heated to 80° C. After stirring for 1 hour the vessel was allowed to cool down to room temperature and depressurized.

The reaction mixture was filtered over $SiO_2$, and concentrated in vacuo. Kugelrohr distillation under vacuum afforded 1.08 g (99% yield) of benzyl alcohol as colourless liquid.

Example 19: Hydrogenation of Furfural

Furfural was hydrogenated according to Example 18 and afforded 0.95 g furfuryl alcohol (99%) as pale yellow liquid.

Example 20: Hydrogenation of 5-(Hydroxymethyl)furfural 5-(hydroxymethyl)furfural was hydrogenated according to Example 18, with a catalyst amount of 0.5 mol % and a base amount of 5 mol %. The hydrogenation afforded 1.20 g (93%) of 2,5-di(hydroxylmethyl)furan as a white crystalline solid.

Example 21: Hydrogenation of 3-(2-Furyl)acrolein 3-(2-Furyl)acrolein was hydrogenated according to Example 18 and afforded 1.23 g 3-(2-furyl)-2-propen-1-ol (99% yield) as colourless oil (mixture of isomers).

Example 22: Hydrogenation of 1-Cyclohexene-1-carboxaldehyde

1-Cyclohexene-1-carboxaldehyde was hydrogenated according to Example 18 and afforded 1.1 g 1-cyclohexene-1-methanol (99% yield) as colourless oil.

Example 23: Hydrogenation of Cinnamaldehyde

Cinnamaldehyde (F) was hydrogenated according to Example 18 using 25 mmol of substrate, and 50 mL of isopropanol. The resulting yellow oil was purified by column chromatography (SiO2; n-pentane:ethyl acetate 4:1), yielding 3.16 g (94%) of cinnamyl alcohol as white crystals.

Example 24: Hydrogenation of Perillaldehyde

Perillaldehyde was hydrogenated according to Example 18. The product was isolated by column chromatography (SiO2; heptane:ethyl acetate 5:1), yielding 1.48 g (96%) of perillyl alcohol as a colourless liquid.

1H NMR (300 MHz, $CDCl_3$): δ 5.63 (broad, 1H), 4.65 (m, 2H), 3.93 (s, 2H), 2.10-1.70 (m, 5H), 1.67 (s, 3H), 1.50 (s, broad, 1H), 1.43 (m, 1H). 13C NMR (75 MHz, CDCl3): δ 149.8, 137.2, 122.4, 108.6, 67.2, 41.1, 30.4, 27.5, 26.1, 20.8. HRMS (ESI+): calculated for C10H16O: 153.12739 (M+H); found 153.12757 (M+H)+, 175.10946 (M+Na)+.

Example 25: Hydrogenation of 4,5,6,7-tetrahydro-4-benzofuranone 4,5,6,7-tetrahydro-4-benzofuranone was hydrogenated according to Example 18, affording 1.37 g (99%) of 4,5,6,7-tetrahydro-4-benzofuranol as a colourless liquid. $^1$H-NMR (300 MHz, $CDCl_3$): δ 7.31 (m, 1H), 6.44 (d, $J_{H-H}$=2.0, 1H), 4.77 (t, $J_{H-H}$=4.4, 1H), 2.60 (m, 2H), 2.09-1.81 (m, 5H). $^{13}$C NMR (75 MHz, $CDCl_3$): δ 152.6, 141.1, 120.0, 109.1, 64.1, 32.7, 23.0, 19.0. HRMS (ESI+): calculated for $C_8H_{10}O_2$: 139.07536 (M+H); found 139.07548 (M+H), 161.05749 (M+Na).

Example 26: Hydrogenation of 4-(2-Furanyl)-3-buten-2-one 4-(2-Furanyl)-3-buten-2-one was hydrogenated according to Example 18, affording 1.28 g (93%) of 4-(2-furanyl)-3-buten-2-ol.

1H NMR (300 MHz, $CD_2Cl_2$): δ 7.38 (d, $J_{H-H}$=1.8, 1H), 6.41 (m, 2H), 6.26 (m, 2H), 4.49 (qd, $J_{H-H}$=6.3, 1H), 2.06 (s, broad, 1H), 1.38 (d, $J_{H-H}$=6.6, 3H). 13C NMR (75 MHz, $CD_2Cl_2$): δ 152.4, 141.9, 132.3, 117.7, 111.3, 108.0, 68.4, 23.4. HRMS (ESI+): calculated for C8H10O2: 161.0573 (M+Na); found 161.05774 (M+Na).

Example 27: Hydrogenation of 1-(1-Cyclohexen-1-yl)-ethanone 1-(1-Cyclohexen-1-yl)-ethanone was hydrogenated according to Example 18, affording 1.25 g (99%) of α-methyl-1-cyclohexene-1-methanol as a colourless liquid.

$^1$H NMR (300 MHz, CDCl$_3$): δ 5.57 (s, broad, 1H), 4.06 (q, $J_{H-H}$=6.3, 1H), 2.15 (s, 1H), 1.93 (m, 4H), 1.53 (m, 4H), 1.16 (d, $J_{H-H}$=6.3, 3H). $^{13}$C NMR (75 MHz, CDCl$_3$): δ 141.3, 121.3, 72.0, 24.9, 23.6, 22.6, 22.6, 21.5. HRMS (ESI+): calculated for C$_8$H$_{14}$O: 149.09369 (M+Na); found 149.09364 (M+Na).

The invention claimed is:

1. A process of production of a compound of formula (IIa):

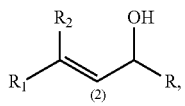

(IIa)

wherein

R is H or a C$_1$-C$_4$ alkyl group, or

R forms together with carbon atom (2) a 4 to 8 membered aliphatic ring system, which can be substituted;

R$_1$ is H; an aromatic ring system which is unsubstituted or an aromatic ring system which is substituted; a heteroaromatic ring system which is unsubstituted or a heteroaromatic ring system which is substituted; an aliphatic ring system which is unsubstituted or an aliphatic ring system which is substituted; a heteroaliphatic ring system which is unsubstituted or a heteroaliphatic ring system which is substituted; —CH$_3$; —CH$_2$CH$_3$; a C$_3$-C$_{10}$ alkyl group, which can be linear or branched and which can be partially unsaturated; or a C$_{11}$-C$_{20}$ alkyl group, which can be linear or branched and which can be partially unsaturated; or R$_1$ forms together with the C—C double bond of formula (IIa) a substituted or unsubstituted 5 to 8 membered aliphatic ring system, a substituted or unsubstituted 5 to 8 membered aromatic ring system, or a substituted or unsubstituted 5 to 8 membered heteroaliphatic ring system, and R$_2$ is H; —CH$_3$; —CH$_2$CH$_3$; or a C$_3$-C$_{10}$ alkyl group, which can be linear or branched and which can be partially unsaturated, wherein the process comprises conducting a selective reduction of a compound of formula (I):

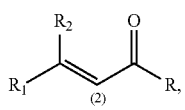

(I)

wherein

R, R$_1$ and R$_2$ have the same meaning as defined in the compound of formula (IIa), in the presence of at least one transition metal catalyst of formula (III):

[M(L)(X)$_a$(L')$_b$],  (III)

wherein

M is a transition metal,

X is an anion,

L' is a monodentate ligand, and

L is a tridentate ligand of formula (IV):

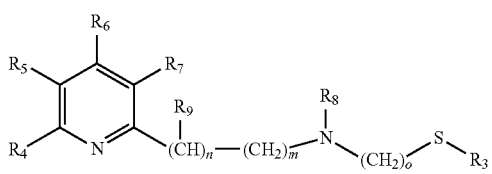

(IV)

wherein

R$_3$ is a linear C$_1$-C$_4$ alkyl group, which can be substituted; a branched C$_3$-C$_4$ alkyl group, which can be substituted; or a phenyl group, which can be substituted, R$_4$ is H; a linear C$_1$-C$_4$ alkyl group, which can be substituted; a branched C$_3$-C$_4$ alkyl group, which can be substituted; or OC$_1$-C$_2$alkyl, R5 is H; a linear C$_1$-C$_4$ alkyl group, which can be substituted; a branched C$_3$-C$_4$ alkyl group, which can be substituted; or OC$_1$-C$_2$alkyl, or R$_4$ and R$_5$ form a C$_4$-C$_8$ ring system, which can be aliphatic or aromatic, R$_6$ is H; a linear C$_1$-C$_4$ alkyl group, which can be substituted; a branched C$_3$-C$_4$ alkyl group, which can be substituted; or OC$_1$-C$_2$alkyl, R$_7$ is H; a linear C$_1$-C$_4$ alkyl group, which can be substituted; a branched C$_3$-C$_4$ alkyl group, which can be substituted; or OC$_1$-C$_2$alkyl, R$_8$ is H or a a linear C$_1$-C$_4$ alkyl group, which can be substituted; a branched C$_3$-C$_4$ alkyl group, which can be substituted, R$_9$ is —CH$_3$ or —CH$_2$CH$_3$, m is 0, 1 or 2, and n is 0, 1 or 2, with the proviso that the sum of m+n is 1 or 2, o is 2 or 3, a is 0, 1, 2, or 3, b is 0, 1, 2, or 3, and with the proviso that the sum of a+b is 2, 3 or 4.

2. The process according to claim 1, wherein the process is carried out in the presence of at least one base.

3. The process according to claim 1, wherein the process is carried out in the presence of at least one base of formula (VIII):

M$^1$(OC$_1$-C$_5$alkyl)  (VIII), wherein

M$^1$ is an alkali metal.

4. The process according to claim 1, wherein the process is carried out in the presence of at least one base of formula (VIII'):

M$^1$(OC$_3$-C$_5$alkyl)  (VIII'), wherein

M$^1$ is Li, Na or K.

5. The process according to claim 1, wherein the process is carried out in the presence of at least one base selected from the group consisting of KOtBu, NaOtBu and LiOtBu.

6. The process according to claim 1, wherein the selective reduction is carried out in the presence of the catalyst of formula (III):

[M(L)(X)$_a$(L')$_b$],  (III)

wherein

M is a transition metal chosen from the group consisting of Os, Co, Ru and Fe, and X is a halogen anion, a carboxylate, borohydride, hydride, BF$_4^-$ or PF$_6^-$, and L' is a monodentate phosphine ligand, and L is a tridentate ligand of formula (IV):

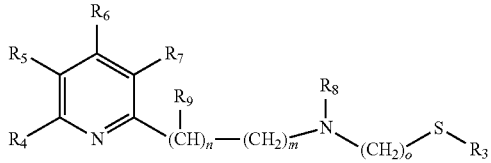

wherein
R$_3$ is —CH$_3$ or —CH$_2$CH$_3$,
R$_4$ is H; —CH$_3^-$; —CH$_2$CH$_3^-$; —OCH$_3$ or —OCH$_2$CH$_3$,
R$_5$ is H; —CH$_3^-$; —CH$_2$CH$_3^-$; —OCH$_3$ or —OCH$_2$CH$_3$, or
R$_4$, and R$_5$ form a C$_4$-C$_8$ ring system, which can be aliphatic or aromatic,
R$_6$ is H; —CH$_3^-$; —CH$_2$CH$_3^-$; —OCH$_3$ or —OCH$_2$CH$_3$,
R$_7$ is H; —CH$_3^-$; —CH$_2$CH$_3^-$; —OCH$_3$ or —OCH$_2$CH$_3$,
R$_8$ is H; —CH$_3$ or —CH$_2$CH$_3$,
R$_9$ is —CH$_3$ or —CH$_2$CH$_3$,
m is 0, 1 or 2, and
n is 0, 1 or 2,
with the proviso that the sum of m+n is 1 or 2,
o is 2 or 3,
a is 0, 1, 2, or 3, and
b is 0, 1, 2, or 3,
with the proviso that the sum of a+b is 2 or 3.

7. The process according to claim 1, wherein the catalyst is a catalyst of formula (III')

$$M(L)(X)_2(L'), \qquad (III')$$

wherein
M is Ru or Fe,
X is Cl$^{31}$,
L' is PPh$_3$, and
L is a tridentate ligand selected from the group consisting of the ligands of formulae (IVa)-(IVl):

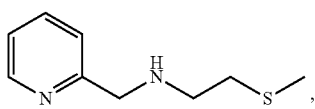 (IVa)

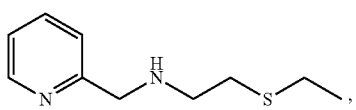 (IVb)

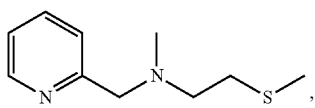 (IVc)

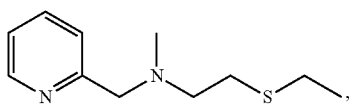 (IVd)

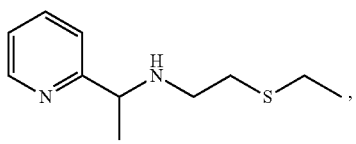 (IVe)

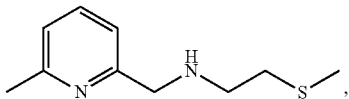 (IVf)

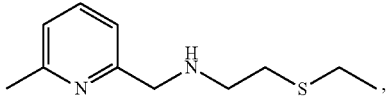 (IVg)

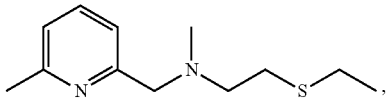 (IVh)

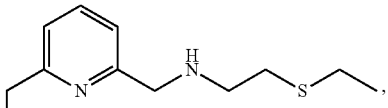 (IVi)

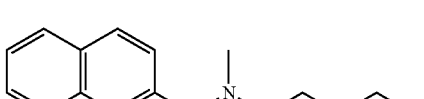 (IVj)

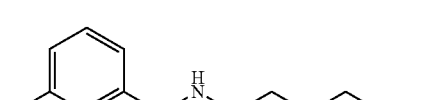 (IVk)

, and (IVl)

[quinoline-CH$_2$-NH-CH$_2$CH$_2$-S-CH$_2$CH$_3$ structure],

8. The process according to claim 1, wherein the catalyst of formula (III) is used in an amount of 0.001 -0.5 mol-%, based on the number of moles of the compounds of formula (I).

9. The process according to claim 1, wherein the reduction is a transfer hydrogenation.

10. The process according to claim 1, wherein the process is carried out with H$_2$ gas.

11. The process according to claim 10, wherein the process is carried out at a pressure of 10 to 50 bar.

12. The process according to claim 1, wherein the process is carried out at an elevated temperature.

13. The process according to claim 12, wherein the elevated temperature is 30-150° C.

14. The process according to claim 6, wherein X in the catalyst of formula (III) is an acetate, a benzoate or BH$_4$–.

15. A catalyst of formula (III):

$$[M(L)(X)_a(L')_b], \qquad (III)$$

wherein
M is a transition metal chosen from the group consisting of Ru and Fe, and
X is a halogen anion, and
L' is triphenylphosphine, and L is a tridentate ligand of formula (IV)

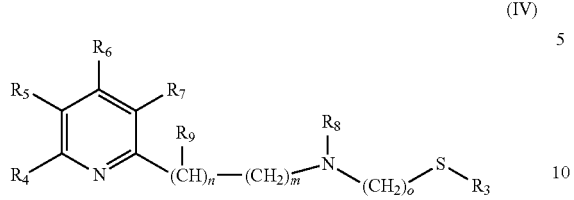

wherein
R$_3$ is —CH$_3$ or —CH$_2$CH$_3$,
R$_4$ is H; —CH$_3$; —CH$_2$CH$_3$; —OCH$_3$ or —OCH$_2$CH$_3$,
R$_5$ is H or —CH$_3$, or
R$_4$, and R$_5$ form a C$_4$-C$_8$ ring system, which can be aliphatic or aromatic,
R$_6$ is H or —CH$_3$,
R$_7$ is H or —CH$_3$,
R$_8$ is H or —CH$_3$,
R$_9$ is —CH$_3$,
m is 0 or 1, and
n is 0 or 1,
with the proviso that the sum of m+n is 1,
o is 2,
a is 1 or 2,
b is 1 or 2,
with the proviso that the sum of a+b is 3.

16. The catalyst according to claim 15, wherein X in formula (III) is Cl$^-$.

17. A catalyst of formula (III'):

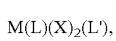

wherein
M is Ru or Fe,
X is Cl$^-$,
L' is PPh$_3$, and
L is a tridentate ligand selected from the group consisting of the ligands of formulae (IVa)-(IVl):

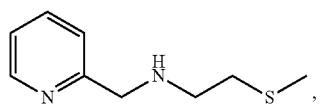
(IVa)

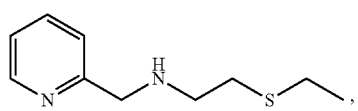
(IVb)

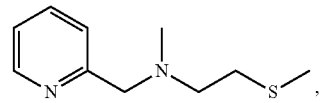
(IVc)

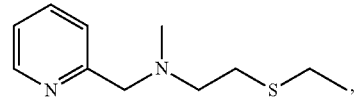
(IVd)

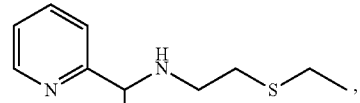
(IVe)

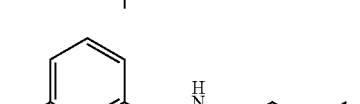
(IVf)

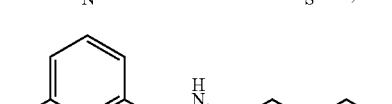
(IVg)

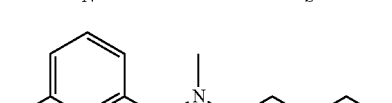
(IVh)

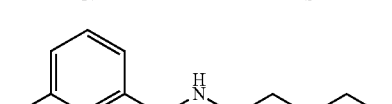
(IVi)

(IVj)

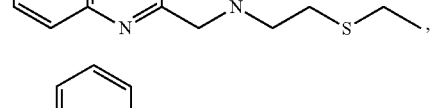
(IVk)

, and (IVl)

.

* * * * *